United States Patent
Eguchi et al.

(10) Patent No.: US 7,531,346 B2
(45) Date of Patent: May 12, 2009

(54) DECOLORIZED YEAST CELL WALL FRACTION

(75) Inventors: Takahiro Eguchi, Takasaki (JP); Tomohiko Nakamura, Takasaki (JP); Syunichi Gomi, Nobeoka (JP); Rika Matsumoto, Nobeoka (JP)

(73) Assignees: Kirin Beer Kabushiki Kaisha, Tokyo (JP); Asahi Kasei Chemicals Corporation, Tokyo (JP)

( * ) Notice: Subject to any disclaimer, the term of this patent is extended or adjusted under 35 U.S.C. 154(b) by 387 days.

(21) Appl. No.: 10/525,022

(22) PCT Filed: Aug. 21, 2003

(86) PCT No.: PCT/JP03/10595

§ 371 (c)(1),
(2), (4) Date: Oct. 6, 2005

(87) PCT Pub. No.: WO2004/018650

PCT Pub. Date: Mar. 4, 2004

(65) Prior Publication Data

US 2006/0110402 A1    May 25, 2006

(30) Foreign Application Priority Data

Aug. 21, 2002  (JP) ............... 2002-241252
Jun. 18, 2003  (JP) ............... 2003-174079

(51) Int. Cl.
*A61K 36/06*   (2006.01)
*C12N 1/18*    (2006.01)
*A23L 1/277*   (2006.01)

(52) U.S. Cl. ............ 435/254.1; 435/410; 426/253; 426/261

(58) Field of Classification Search ........... 435/251.1, 435/410; 426/253, 261
See application file for complete search history.

(56) References Cited

U.S. PATENT DOCUMENTS

| 7,238,355 | B1 * | 7/2007 | Kasai et al. ............ 424/195.16 |
| 2004/0071732 | A1 | 4/2004 | Kasai et al. |

FOREIGN PATENT DOCUMENTS

| EP | 0 566 347 A2 | 10/1993 |
| JP | 4-248968 | 4/1992 |
| JP | 6-504191 | 5/1994 |
| JP | 08-041218 | 2/1996 |
| JP | 2000-44878 | 2/2000 |
| JP | 2000-316523 | 11/2000 |
| JP | 2002-53807 | 2/2002 |
| JP | 2003-70428 | 3/2003 |

* cited by examiner

*Primary Examiner*—Jon P Weber
*Assistant Examiner*—Kailash C Srivastava
(74) *Attorney, Agent, or Firm*—Foley & Lardner LLP

(57) ABSTRACT

The yeast cell wall fraction comprising cell residues obtained by removing internal soluble components from enzyme-treated yeast, or cell residues obtained by treating the cell residues with acid solution and removing the acid solution-soluble components. By decolorizing the residues with a decolorizing agent, the decolorized yeast cell wall fractions to which excellent physical properties are added, are obtained without impairing the excellent properties of the yeast cell wall fractions before the decolorization. The decolorized yeast cell wall fractions of the present invention have a white color and retain the merit of the yeast cell wall fractions before the decolorization for the use as a coating agent. Further, excellent properties such as the mechanical properties of the yeast cell wall fractions being enhanced and the yeast odor being decreased, are added to the decolorized yeast cell wall fractions.

7 Claims, 2 Drawing Sheets

A: film unformed              B: film formed

A (Example Item 1) (×20K)

B (Example Item 3) (×10K)

C (Comparative Example Item 1) (×20K)

D (Comparative Example Item 3) (×10K)

DECOLORIZED YEAST CELL WALL FRACTION

This application is a National Stage application of PCT/JP2003/010595, filed Aug. 21, 2003, which claims priority from Japan patent applications 2002-241252, filed Aug. 21, 2002 and 2003-174079, filed Jun. 18, 2003. The entire contents of each of the aforementioned applications are incorporated herein by reference.

TECHNICAL FIELD

The present invention relates to a decolorized yeast cell wall fraction, which has been decolorized and deodorized, and has improved properties, a method for preparing the same, and a use of the decolorized yeast cell wall fraction as a coating agent.

BACKGROUND ART

Conventionally, as for the use of yeast cell wall fraction, attempts have been made to develop film material from yeast. Japanese Patent Publication No. 56-19971, for example, discloses an edible protein film based on water-soluble proteins produced by removing the yeast cell membrane components from residual yeast which was produced by extracting nucleic acid. Japanese Laid-Open Patent Application No. 53-45385 discloses a method for producing a film, wherein the cells of a microorganism such as yeast are heated and alkali treated, acid is added for treatment involving isoelectric precipitation, the pH of the resulting precipitate is adjusted to between 6 and 8, and a plasticizer is added to the resulting gel-forming microorganism cells to produce a constituent.

Further, Publication of Patent No. 3349677 (Japanese Laid-Open Patent Application No. 2000-44878) describes: a coating agent whose primary component comprises yeast cell wall fractions comprising cell residue obtained by removing the internal soluble cell components of enzyme-treated yeast; and also the use of the coating agent or the coating agent comprising a plasticizer as a coating agent or as a coating film. Examples of its excellent properties include that this coating agent is able to coat even in a disperse medium of 100% water, affords a nonsticky finish despite its viscosity, thus resulting in coated particles and/or granules that do not aggregate, and further having a function to control release time. Moreover, it is shown that a film formed from the coating agent has a property that it has an extremely low oxygen permeability coefficient under dried conditions.

However, the coating agent described in Publication of U.S. Pat. No. 3,349,677 has an extremely excellent film property, when the film coating agent described in the patent publication is used, as it has a color of yellow-brown to brown, the coating agent or the making tablet agent has a bad-looking compared to the substances to be wrapped, changes of properties can be misidentified (for example, mistaken as mold, or mistaken the color to degradation etc.), and therefore result to delay of detecting deterioration.

Moreover, regarding the coating agent described in the patent publication, as the yeast cell wall fraction itself comprises relatively many proteins (21% as weight ratio), or lipid (8.0% as weight ratio), colorization due to oxidation of lipid and the like during preservation could happen.

Furthermore, the yeast cell wall fraction itself has some odor derived from yeast (hereinafter mentioned as yeast odor), therefore when the coating is made for flavor components, while maintaining the intended flavor component on one side, there was a risk that the flavor necessary was masked or impaired by the yeast odor of the yeast cell wall fraction itself. Thus, it was necessary to limit the additive level low and there was a problem that sufficient ability could not be exerted.

Further, as a mechanical property of the film itself, it is inferior for flexibility (plasticity), and relatively brittle. In some combinations of substances to be wrapped, films happened to be breakable due to environmental changes such as outer humidity.

On the other hand, when using the yeast cell wall fraction, it is already known to decolorize/deodorize the yeast cell wall fraction. In the Japanese Laid-Open Patent Application No. 4-248968, a method for treating yeast extract residue with alkali and acid, then decolorize with ozone and to treat with ethanol before and after the ozone treatment is described. Japanese Laid-Open Patent Publication No. 6-504191 discloses a method for treating yeast residue being acidified after treatment with alkali, hydrogen peroxide and the like, and its treated substances; U.S. Pat. No. 3,407,125 (Japanese Laid-Open Patent Application No. 9-103266) discloses a method for treating yeast autolytic insoluble substance with alkali, after suspending the substances with ethanol.

However, with these conventional methods, when the treatment for decolorization/deodorization is performed, the treated substances could be degenerated and loose their properties, or the film property or the film disintegrating property could be lost if the original form and structure are changed. Moreover, if it is decolorized while maintaining the film property or film disintegrating property, it could happen that it could not be decolorized to the intended level, and so on. Therefore, there were various limits for its use.

As for decolorization and deodorization of yeast extract residue and the like, attempts have been made conventionally. However, when the conventionally-performed methods of decolorization, described in for example, Japanese Laid-Open Patent Application No. 4-248968 (method of decolorizing and deodorizing yeast extract residue), Japanese Laid-Open Patent Application No. 6-70751 (yeast fragment product) or in Published Japanese Translation of PCT International Publication No. 6-504191 (treatment of yeast residue and products obtained thereof), that is methods for conducting heating treatment under high-alkaline condition (including reflux boiling etc.) or heating treatment under highly-acid condition (including reflux boiling etc.), removing soluble components and the like, and treating with agents such as hydrogen peroxide or reacting with ozone and the like, or reacting bleaching agents such as hypochlorous acid, are directly applied to the decolorization treatment of yeast cell wall fraction, there was a problem that the excellent property of the yeast cell wall fraction as described above is abolished in the obtained decolorized yeast cell wall fractions.

On the other hand, as for pharmaceutical, it is rare that drug component is directly administered in the form of chemical compound, and dosage forms are prepared by compounding pharmaceutical additives to dissolute drug component according to its purpose. There are various pharmaceutical additives, and one of them is exemplified.

For example, EUDRAGIT LS30-D55 used as an aqueous coating agent for medical use had problems to be a non-natural substance, with low gas-barrier property, and that film disintegration property is worse when the coating level was increased. Therefore, an aqueous coating agent from natural product, having high gas-barrier property, effect for preventing volatilization of perfume component, odor and the like, and sufficient disintegration property was awaited. Furthermore, the yeast cell wall fraction of the Patent Publication No.

3349677 is aqueous, derived from natural substance, having high gas-barrier property, film property, and good film-disintegration property, but as it has a color and odor of yeast, one without color and odor was awaited. Moreover, for HPC or HPMC used for binder, when the added level is increased, disintegration of granulation could be delayed. The yeast cell wall fractions show strong binding when dried, while showing rapid disintegration in water, therefore it is a disintegrated agent having binding ability. However, as it shows a color of yellow-brown to brown, the resulting granulation would have a color yellow-brown to brown. Therefore a colorless one was awaited.

Moreover, as a capsule substrate, gelatin, water-soluble polymer (hydroxymethyl ethyl cellulose), pullulan, polyvinyl alcohol (PVA) and the like are known, but they have problems such as difficulties in control release, deterioration of agents due to low oxygen-barrier property, safety of material (BSE or synthetic compounds) and the like.

As for resolving these problems, attempts to use yeast cell wall fractions as capsule substrate were made, and were described in Japanese Laid-Open Patent Application Nos. 2002-38133 and 2003-70428. However, in these methods, as yeast cell wall fraction has a color of yellow-brown to brown, there were problems that the resulting capsules would be yellow-brown to brown, or that the yeast cell wall fraction itself was colored as many proteins or lipids were contained in the yeast cell wall fraction.

The object of the present invention is to provide a decolorized yeast cell wall fraction being decolorized and deodorized, wherein the color and odor from yeast cell wall fraction have been removed, having excellent film property, preferably having physical properties that film disintegration property and excellent gas barrier property of the formed film have been maintained and improved, a method for producing the same, use of the decolorized yeast cell wall fraction as a coating agent, and further a coated material treated with the coating agent, and the like.

Yeast cell wall fractions such as yeast cell wall fraction (YCW) comprising cell residue obtained by removing the internal soluble cell components of enzyme-treated yeast, or acid-treated yeast cell wall fractions (AYC) comprising cell residue obtained by further treating the cell residue with acid solution, and removing acid solution-soluble components (hereinafter, yeast cell wall fractions (YCW) and acid-treated yeast cell wall fractions (ACW) are described collectively as yeast cell wall, not otherwise specified), have excellent physical properties as they have an excellent film property, and the film formed with these fractions have gas-barrier property. However, due to the coloring of yellow-brown to brown and to the typical odor and the like derived from yeast, the color, odor and the like could be an obstacle for the use as pharmaceuticals, foods and the like.

The present inventors have made a keen study to resolve the above-mentioned objects, and decolorized yeast cell wall fractions such as cell residue obtained by removing internal soluble cell components from enzyme-treated yeast, or cell residue obtained by further treating the cell residue with acid solution, and removing the acid solution-soluble components, removed the color and odor derived from yeast cell wall fraction without impairing excellent properties of the yeast cell wall fraction, such as film property and gas-barrier property of the formed film, and obtained a decolorized yeast cell wall fraction whose liquid YI (Yellow Index) is low (13 or under), and which has film property, and more preferably film disintegration property and they have found that a decolorized yeast cell wall fraction capable of preventing deterioration and the like of the coated material can be obtained by that treatment when the decolorized yeast cell wall fraction is used as a coating agent. Thus, the present invention has been completed.

The decolorized yeast cell wall fraction of the present invention can be used as an excellent coating agent, for example by exerting effectiveness also as inhibitor of volatilization and sublimation of agents containing volatilizing or sublimating substances, being a problem of "generation of whisker" in the field of medicinal preparation. "Whisker" herein mentioned relates to a phenomenon wherein volatilizing/sublimating substances in the solid preparation volatilize, and deposit spicular crystals on the surface of the solid preparation. When this phenomenon occurs, problems such as degradation of fluidity of the solid preparation or misconception with mold are pointed out.

DISCLOSURE OF THE INVENTION

In other words, the present invention relates to a decolorized yeast cell wall fraction whose yellow index (YI) of the liquid measured by a reflective method with the use of SE-2000 of Nippon Denshoku (illumination C, field of view 2 degree) is 13 or less ("1"); the decolorized yeast cell wall fraction according to "1", wherein the decolorized yeast cell wall fraction has a property to form continuous film whose oxygen permeability is 250 ml/$m^2 \cdot d \cdot$MPa or less at a humidity of 60% RH, when 5% slurry (weight ratio) of the decolorized yeast cell wall fraction is casted using a baker applicator, on a drawn-polypropylene film Senesi-POP (Daicel Chemical Industries; thickness of film membrane 0.02 mm), dried for 45 min in an oven at 60° C. to make a cast film (thickness of film membrane approximately 0.015 mm) ("2"); the decolorized yeast cell wall fraction according to "1" or "2", wherein the disintegration time of the film in pure water is within 60 min, when 5% slurry (weight ratio) of the decolorized yeast cell wall is dried for 2 hours at 60° C., in a circular container (diameter of 60 mm) to make a cast film (thickness of film membrane: approximately 0.1 mm) ("3"); the decolorized yeast cell wall fraction according to any one of "1" to "3", wherein the fraction is prepared by decolorizing cell residue which is obtained by removing internal soluble cell components from enzyme-treated yeast, or cell residue which is obtained by further treating the cell residue with acid solution, and removing acid solution-soluble components ("4").

Further, the present invention relates to a method for producing the decolorized yeast cell wall according to any one of "1" to "4", wherein the fraction is prepared by decolorizing cell residue which is obtained by removing internal soluble cell components from enzyme-treated yeast, or cell residue which is obtained by further treating the cell residue with acid solution, and removing acid solution-soluble components, by using a decolorizing agent ("5"); the method for producing the decolorized yeast cell wall fraction according to "5", wherein the decolorizing treatment by using a decolorizing agent is a decolorizing treatment with hydrogen peroxide and ozone ("6").

Moreover, the present invention relates to a coating agent whose primary component is the decolorized yeast cell wall fraction according to any one of "1" to "4" ("7"); a coated material wherein a coating treatment is carried out with a coating agent whose primary component is the decolorized yeast cell wall according to "7"; the coating material according to "8", wherein the coated material is a microparticle, a granule or a tablet; or the coated material according to "8" or "9", wherein the coating material is a medicinal preparation or food.

BEST MODE OF CARRYING OUT THE INVENTION

Figure 1:
FIG. 1 is a set of pictures that shows the results of film forming test from the decolorized yeast cell wall fraction in the example of the present invention. "A" shows the result of the formation test of Comparative Example Item 4 (film forming property), "B" shows the result of the film forming test of Example Item 1 (film forming property).
Figure 1:

The present invention relates to a decolorized yeast cell wall fraction produced by decolorizing with the use of decolorizing agents a yeast cell wall fraction comprising cell residue which is obtained by removing internal soluble cell components from enzyme-treated yeast, or an acid-treated yeast cell wall fraction comprising cell residue which is obtained by further treating the cell residue with acid solution and removing acid solution-soluble components. The decolorized yeast cell wall fraction is decolorized and deodorized, the YI (Yellow Index) of the liquid is low (13 or less), and has film property. More preferably, it has excellent properties such as film disintegration property, gas-barrier property of the formed film, and other physical properties. The decolorized yeast cell wall fraction of the present invention exhibits excellent properties when used as a coating agent.

[Property of the Decolorized Yeast Cell Wall Fraction]

The decolorized yeast cell wall fraction of the present invention has excellent properties as follows:

(Yellow Index: YI)

The decolorization level of the decolorized yeast cell wall fraction of the present invention is determined by YI level. In the present invention, YI level is defined as "YI (Yellow index) of the liquid determined by a Reflective method (illumination C, field of view 2 degree) with the use of SE-2000 of Nippon Denshoku".

In other words, as the yeast cell wall fraction has a yeast-derived color of yellow-brown to brown, the decolorization I is shown as a positive level when the color changes from colorless or white to yellow direction, as it is defined in JIS K 7103. The lower YI is, the higher the white index is (yellow index is lower). For example, in a solution of 5% solid content of decolorized yeast cell wall fraction (5 g), when YI show a negative level, it means that the decolorization level is high and the yellow index is low, therefore YI is defined to be 0. In the present invention, the determination of color of solution of 5% solid content is performed by a reflective measuring method with the use of Spectrophotometer SE-2000 of Nippon Denshoku, at illumination C, field of view 2 degree, and the mean value of triplicate is shown. The liquid YI of the decolorized yeast cell wall fraction of the present invention is 13 or less. Preferably it is 6 or less, and more preferably 1 or less. As the decolorized yeast cell wall fraction wherein YI is more than 13, has a yellow color, when applied to dosage forms, a difference of color will appear between the drug and other excipients, which is not preferable.

Further, the comparison of yellow index with the existing coating agents can be performed after transforming the agents into a form of tablet (10% coated tablet based on tablet weight) or into a form of film (thickness of about 0.1 mm), by tablet YI or film YI, respectively.

Therefore, the decolorization level of the tablet or film itself can be also evaluated and defined by these tablet YI or film YI.

(Cell Wall Shape Retaining Property)

By observing the decolorized yeast cell wall fraction with a scanning electron microscope (SEM), it was determined whether almost all of the yeast cell wall fractions (70% or more) maintain the original shape of yeast cell or not, among 10-100 yeast cell wall fractions. From the results, those maintaining the original shape were defined as having a cell wall shape retaining property.

Further, the distribution of particle size was measured according to a common method with the use of a particle size distribution analyzer (e.g. laser scanning particle size distribution analyzer LA-920, HORIBA). As relative reflectance, a level so that $\chi^2$ is 0.3 or less is selected, the measurement is performed under insonation to prevent aggregation of particles. The destruction condition of the shape of cell wall was determined according to the shifting of mode diameter of particle size distribution to minute direction.

Moreover, it is preferable that the various manufactured products (film) showed in the following have the intended property. The method for measuring and the definition of various physical properties are as follows.

(Film Property)

5% (weight ratio) slurry of yeast cell wall fraction is casted using a baker applicator (Yoshimitsu Seiki), on a oriented-polypropylene film Senesi-POP (Daicel Chemical Industries; thickness of film membrane 0.02 mm, catalogue oxygen permeability 304 ml/m$^2$·d·MPa), and then dried for 45 min in an oven at 60° C., to make a film (thickness of film membrane 0.015 mm).

The above-mentioned cast film was subjected to an oxygen permeability test under the condition comprising a temperature of 20° C., humidity of 60% RH, a test area of 5 cm$^2$, and an oxygen concentration of 100% with the use of OX-TRAN100 (MOCON: Modern Controls). Oxygen permeability herein mentioned refers to the amount of permeation of oxygen, per film area, per hour, per pressure, when the thickness of the film is determined (thickness about 0.015 mm; thickness of whole film membrane about 0.035 mm). When the oxygen permeability of the film wherein the decolorized yeast cell wall fraction is casted on a oriented-polypropylene film is less than 250 ml/m$^2$·d·MPa (RH60%), it was defined to be a continuous film, having film property.

The present invention should at least meet the requirement concerning the above-mentioned liquid YI and film property, but it is more preferable that it meets various properties such as the following film disintegration property.

(Film Disintegration Property)

The decolorized yeast cell wall fraction of the present invention preferably has an excellent film disintegration property. The film disintegration property of the decolorized yeast cell wall fraction of the present invention is determined by "the disintegration time of the film in pure water, wherein the cast film (thickness of film membrane: about 0.1 mm) is produced by drying 5% slurry (weight ratio) of the decolorized yeast cell wall fraction for 2 hours at 60° C., in a circular container with a diameter of 60 mm."

In other words, "having film disintegration property (water dispersion property)" means that "when an area of 4 cm² of the decolorized yeast cell wall fraction of a cast film (thickness of film membrane: about 0.1 mm) produced by drying a 5% slurry (weight ratio) of the decolorized yeast cell wall fraction for 2 hours is used in a circular container with a diameter of 60 mm at 60° C., with pure water of 37° C. in a disintegration tester described in Japanese Pharmacopoeia, Fourteenth Edition, the film is dispersed into water within 60 min, and no film remnant is observed on a 2.0 mm—opening mesh in the glass tube". The decolorized yeast cell wall fraction of the present invention disintegrates within 60 min, and shows a good film disintegration property (water dispersion property). As the decolorized yeast cell wall fraction of the present invention has a good film disintegration property, when it is used as a coating agent for dosage forms and the like, the drug can be effectively released.

(Film Forming Property)

The film forming property of the present invention relates to that a cast film (thickness of film membrane: 100 μm or less) produced by drying 7-10 g of 5±1% slurry of the decolorized yeast cell wall fraction for 30 min at 120° C. in a circular container with a diameter of 70-100 mm has 3 or less continuous film pieces (as the number of cracks on the surface of the film is small, the number of the continuous film surface wherein the surface is relatively large, and being separated from each other by cracks is 3 or less). On the contrary, the film non-forming property relates to the film that constitutes 4 or more closed surfaces under the same condition (as the number of cracks on the surface of the film is large, the number of the continuous film surface wherein the surface is relatively small, and separated from each other by cracks is 4 or more).

The decolorized yeast cell wall fraction of the present invention has an excellent film forming property. Therefore, when it is used as a coating agent for dosage forms and the like, it has a continuous film shape, and inhibition of the elution of active components or masking of odor can be effectively performed.

(Film Mechanical Property)

10% of glycerin based on dry material is added as a plasticizer to produce a cast film of the decolorized yeast cell wall fraction (thickness of film membrane: 50-100 μm). The above-mentioned film is used to conduct a tensile test, and the tensile strength at break (MPa), the elongation at break (%), strength of tip plunging (N) and the plunged depth (mm) were determined. The tensile strength was tested by making a test piece following JIS Z1702, and according to JIS K7161, K7162, with the use of 2005-type Universal material testing precision machine (Intesco), at a tensile speed of 500 mm/min and the tensile strength, elongation rate were measured and defined as tensile strength and elongation rate. The strength of tip plunging was measured in a film form of a thickness of 50-100 μm, with the use of 2500-type Universal testing precision machine (Intesco), at a test speed of 200 mm/min with a stick having a pointed-tip of ¼ inch, and the load (unit: N) and the plunged depth of the stick (mm) at the time when the film is broken over, were defined as strength of tip plunging (unit: N), respectively. The tensile test was performed at n=5, the tip plunging test was performed at n=3 for each of strength of tip plunging, plunged depth, respectively, and mean values were calculated.

For example, when 10% of plasticizer is added to each of conventional yeast cell wall fraction and decolorized yeast cell wall fraction, it is preferable that various mechanical properties of the decolorized yeast cell wall fraction are enhanced for the load (N) by 1-20 fold, for the plunged depth (mm) by 1-20 fold, and for the strength of tip plunging (N) by 1-20 fold, compared with those of the conventional yeast cell wall fraction. Further, it is preferable that the tensile strength (MPa) is enhanced by 1-20 fold, and for the elongation rate by 1-20 fold.

(Gas-Barrier Property)

The decolorized yeast cell wall fraction of the present invention has an excellent gas-barrier property. The gas barrier property of the decolorized yeast cell wall fraction of the present invention is determined by: "the oxygen permeability under a humidity of 60% RH, when a 5% slurry (weight ratio) of the decolorized yeast cell wall fraction is casted using a baker applicator, on a oriented-polypropylene film Senesi-POP (Daicel Chemical Industries, thickness of film membrane 0.02 mm), and dried for 45 min in an oven at 60° C., to make a cast film (thickness of film membrane about 0.015 mm)."

In other words, in the present invention, as for gas barrier property, when 5% slurry (weight ratio) of the decolorized yeast cell wall fraction is casted on a oriented-polypropylene film Senesi-POP (Daicel Chemical Industries; thickness of film membrane 0.02 mm, oxygen permeability 304 ml/m²·d·MPa) using a baker applicator, dried in an oven at 60° C. for 45 min to make a cast film (thickness of film membrane about 0.015 mm), continuous films showing an oxygen permeability level of 250 ml/m²·d·MPa or less, at a humidity of 60% RH is produced. If continuous films are not produced at this stage, when coating is performed to dosage forms and the like, as the spreading property is lacking, the coating to the stamped-part or edge-part of the tablet will be insufficient, and cracks could occur. Therefore, the function of protecting the content as a coating agent will be impaired, which will become a problem.

(Coloration Property of the Film)

It is preferable that no coloration property of the film is observed for the decolorized yeast cell wall fraction of the present invention. When the YI of the film (thickness of film membrane: about 0.10 mm), made by drying a 5% slurry (weight ratio) of the decolorized yeast cell wall fraction for 2 hours at 60° C. is defined as initial YI, the YI of the film after maintaining the aforementioned film at 40° C. at 75% RH for a month was defined as elapse YI. When the increased YI, that is the difference between the elapse YI and the initial YI, is 5 or more, the film will be colored in yellow-brown and this is defined to have coloration property. It is not preferable that YI is 5 or more, as the drugs will be colored due to the coloration of the yeast cell wall fraction which is coated on tablets and the like.

[Preparation of Cell Residue (Yeast Cell Wall Fraction) by Removing the Internal Soluble Cell Components from Yeast.]

The present invention relates to a decolorized yeast cell wall fraction prepared by decolorizing yeast cell wall fraction comprising cell residue obtained by removing internal soluble cell components from enzyme-treated yeast, or acid-treated yeast cell wall fraction comprising cell residue obtained by treating the cell residue with acid solution and removing acid solution soluble components. Especially, the present invention relates to a decolorized yeast cell wall fraction prepared by decolorizing yeast cell wall fraction comprising the cell residue which is obtained by removing soluble internal cell components from enzyme-treated yeast by washing with organic solvents such as ethyl acetate, toluene, hexane, acetone, ether, petroleum ether and various alcohols (methanol, ethanol, propanol, isopropanol etc.), or a mixture thereof, or with a mixture of water of pH 2-12 and the organic solvents (e.g. a mixture of water of pH 2-12 and ethanol), or acid-treated yeast cell wall fraction comprising cell residue which is obtained by removing acid solution soluble components, without loosing excellent physical properties of the yeast cell wall fraction before the decolorization, and capable of adding excellent properties of the material. As for the above-mentioned organic solvents, preferably hexane, acetone, various alcohols (methanol, ethanol, propanol etc.), and more preferably ethanol can be used. The cell residue which is obtained by removing soluble internal cell components from yeast used in the present invention are prepared as follows.

(Starting Material Yeast)

Any yeast taxonomically belonging to yeasts may be used as the yeast serving as the starting material for the coating agent of the present invention. Examples include brewer's yeast, wine yeast, baker's yeast and torula yeast. More specific examples include *Saccharomyces* species to which brewer's yeast and baker's yeast belong, *Saccharomyces cerevisiae, Saccharomyces pastorianus, Saccharomyces rouxii, Saccharomyces carlsbergensis, Saccharomyces pombe*, or *Candida utilis, Candida tropicalis, Candida lipolytica, Candida flaveri*, and *Candida boidinii* belonging to *Candida* genus that are methylotrophic yeast, and further *Rhodotrura minuta*.

(Aspects of Yeast to be Used)

Such yeasts can be used alone or in combination. The use of live yeast is preferred, although yeasts in configurations other than live yeast such as dried yeast can also be used, and can, for example, be treated in the same manner as live yeast by being suspended in water or the like. The size or configuration of the yeast that is used is not particularly limited, although the configuration is preferably as close as possible to spherical, and the size preferably ranges from 1 to 20 μm.

(Removal of Internal Soluble Cell Components)

Yeasts contain water—or polar solvent—soluble internal cell components such as proteins, amino acids, saccharides, nucleic acids, and organic acids. Such internal cell components are readily solubilized in water, and yeast cell wall fraction after removal of these internal soluble cell components are preferably used. If the internal soluble cell components are not removed, film property will worsen (film will be brittle), which is not preferable.

To obtain yeast cell wall fractions by removing such internal soluble cell components from the yeast, it is necessary to solubilize such internal cell components by enzyme treatment to remove them from the cells. Any enzyme treatment or treatment by combining additives such as alcohol and enzyme used during the production, making yeast internal cell components into yeast extract, can be used as the enzyme treatment, such as so-called autolysis featuring the use of the enzymes inside yeast cells; methods for adding enzymes such as proteases, nucleases, β-glucanase, esterases, lipases, phosphatase are added from outside; or combinations of such methods. This allows effective use of the extract residue of yeast extract in the manufacture of common yeast extract, in the form of the yeast cell wall fractions in the present invention.

To speed up the enzyme treatment or the like, before or during the treatment, a high pressure homogenizing treatment (preferably a treatment of less than 6 times at 10-150 MPa) or an ultrasonic treatment (with the use of an ultrasonic oscillator having a maximum amplitude of 50 μm and output of 2 KW at 20 KHz, and with an output of 50-100%, an exposure for 0.01-100 min, preferably with an output of 70% or more, an exposure for 0.01-45 min) can be performed. Moreover, to improve the decolorization efficiency, it is preferable to perform these two treatments in combination. The number of times of pretreatment is not limited as long as it does not have negative effect to the fraction properties (YI, yield etc.), but preferably is less than 10 times, more preferably less than 6 times, most preferably less than 2 times. If performed 10 times or more, shrinking of the film will occur, and it is not preferable as the film property will worsen.

At the completion of the enzyme treatment, the yeast is washed (washing treatment) with organic solvent such as ethyl acetate, toluene, hexane, acetone, ether, petroleum ether, various alcohols (methanol, ethanol, propanol, isopropanol etc.) or a mixture thereof, or with a mixture of water of pH 2-12 and organic solvents (e.g. mixture of water of pH 2-12 and ethanol), and by removing internal soluble cell components by centrifugation and the like after adding water and diluting the enzyme-treated solution, the yeast cell wall fraction as the cell residue is obtained. Further, by carrying out together the dispersion treatment such as the above-mentioned homogenizer or ultrasonic treatment after the enzyme reaction, the removal of unnecessary internal cell components (coloring components, lipid, odor component, protein etc.) can be promoted.

The yeast cell wall fractions thus obtained without any particular chemical treatment consist of a membrane that is relatively durable in physical and chemical terms, consisting of glucan, mannan, and chitin layers, and can thus be used as an excellent coating agent capable of wrapping greater amounts of substances without compromising the function of protecting the substances to be wrapped. However, the yeast cell wall fractions can also be prepared with the incorporation of yeast washing treatment, adjustment of the pH, temperature, or pressure, and the like as needed.

(Acid Solution Treatment and Removal of Acid Solution-Soluble Components)

Next, it is preferable to treat the above-mentioned yeast cell wall fraction obtained by removing the internal soluble components with an acid solution. More specifically, the aforementioned yeast cell wall fractions can be treated with 0.01-2 N, and preferably 0.1-0.5 N, acid such as hydrochloric acid, sulfuric acid, phosphoric acid, or nitric acid, or organic acids such as acetic acid or citric acid, the resulting suspension can be centrifuged or the like to separate the supernatant and yeast cell residue, and the yeast cell residue can be obtained to prepare the acid-treated yeast cell wall fractions. The material is also preferably heated to around 60-80° C. during the acid treatment. Generally, when acid concentration or reaction temperature is too high, it is not preferable as the film property worsens.

[Decolorization Treatment of the Yeast Cell Wall Fractions]

(Decolorization Treatment)

By performing decolorization (or bleaching) treatment to the above-mentioned yeast cell wall fractions, the specific color of yellow-brown to brown of the untreated yeast cell wall fraction will disappear, and whitened fractions will be generated. As for decolorization (or bleaching) treatment, common decolorizing (bleaching) agents such as oxidative decolorizing treatment using hypochlorous acid bleaching agent, hydrogen peroxide, ozone, dioxide chlorine, hypercarbonic acid, or hyperacetic acid and the like; reductive decolorizing treatment using sulfite reduction and the like can be used. Such treatments using decolorizing (or bleaching) agents can be conducted separately or by combining plural methods appropriately. Among these methods, treatments by ozone or hydrogen peroxide are preferable from the point of view of danger caused by residues of chemical agents used, difficulty of removal of residue, residual odor, or the like. The number of times or order of the decolorization treatments are not specifically limited. However, when ozone and hydrogen peroxide are used separately for the decolorization treatment, it is preferable that ozone is firstly used and then hydrogen peroxide, as the YI of the obtained product or of the manufactured product is good, thus preferable from the point of film property, more preferable from the point of film disintegrating property when the decolorized yeast cell wall fraction is used as a coating agent. Further, both treatments can be performed under alkaline condition, or a whole or a part of the alkaline treatment performed between the two decolorizing treatments can be separated and performed in the order of (1) ozone treatment, alkaline treatment, hydrogen peroxide treatment; (2) ozone treatment, alkaline treatment, hydrogen peroxide treatment under alkaline condition; (3) ozone treatment under alkaline condition, alkaline treatment, hydrogen peroxide treatment; (4) ozone treatment under alkaline condition, alkaline treatment, hydrogen peroxide treatment under alkaline condition. Moreover, when the hydrogen peroxide treatment is firstly performed, it can be performed in the order of (5) hydrogen peroxide treatment, alkaline treatment, ozone treatment; (6) hydrogen peroxide treatment, alkaline treatment, ozone treatment under alkaline condition; (7) hydrogen peroxide treatment under alkaline condition, alkaline treatment, ozone treatment; (8) hydrogen peroxide treatment under alkaline treatment, alkaline treatment, ozone treatment under alkaline condition.

Ozone treatment is performed by, for example, treating slurry of yeast cell wall fraction at a concentration of 0.1-10%, under an ozone mixed gas condition at a concentration of 1000-100000 ppm generated with an ozone-generating machine, preferably performing a contact reaction at 1000-100000 ppm as fine bubbles. More specifically, it is preferable to perform the reaction with an injecting level of 0.01-10 g ozone/(g decolorized object.hr) for 1-24 hours. The maximum level of ozone concentration of this ozone reaction condition is determined by the ability of the current ozone-generating machine. When the ozone purity increases, the reaction efficiency increases more. Therefore, there is generally no regulation for the maximum level of concentration. However, a concentration of 0.1% or less is not preferable as YI will be high. As for the decolorized yeast cell wall fraction obtained by ozone treatment, a color reversion will occur and will be recolored to burned umber, it is preferable to perform an alkaline treatment (adjust a slurry after decolorization reaction to pH 7-13 with alkaline solution such as sodium hydroxide), centrifugation (4200 rpm, 10 min) and water washing. To degrade the remaining ozone, it is preferable to perform by verifying the remaining ozone with a peroxide check strip (e.g. Merckoquant Peroxide-Test, etc.) to regulate the addition level of the reducing agent.

As for hydrogen peroxide treatment, it is preferable to perform the reaction by regulating the slurry concentration to 0.1-10%, the temperature to 20-120° C., under alkaline condition (pH 7.0-13.0) for 0.1-30 hours, more preferably by regulating the hydrogen peroxide concentration to 0.5-5%, the temperature at 40-80° C., at pH 8.5-11.5 for 1-20 hours. However, a concentration of 0.1% or less is not preferable as YI will be high. To remove the remaining hydrogen peroxide, it is preferable to perform catalase treatment (e.g. REYONET F PLUS; Nagase Chemtex) (treatment condition: pH 3.0-8.5, temperature 10-50° C.), treatment for inactivating the enzyme by decreasing pH (pH2 or less) according to need, and further by heat treatment, or treatment for reducing sulfurous acid and the like. The remaining hydrogen peroxide is preferably checked by confirming the process with a peroxide check strip (e.g. Merckoquant Peroxide-Test, etc.) and the like, and by adding reducing agent and catalase level as needed.

To remove the lipid of the decolorized yeast cell wall fraction and the lipid peroxide generated by the decolorizing reaction, it is preferable to water-wash by centrifugation, after the decolorizing treatment. Further, it is preferable to wash with organic solvents (ethylacetate, toluene, hexane, acetone, ether, petroleum ether, methanol, ethanol, propanol, isopropanol, etc.). This washing treatment with organic solvents is preferable as it will reduce the reactivity of the yeast cell wall fraction itself and the reactivity with the drug to be coated.

Moreover, by replacing the water where the yeast cell wall fraction is dispersed in a slurry form, with the organic solvents (ethyl acetate, toluene, hexane, acetone, ether, petroleum ether, methanol, ethanol, propanol, isopropanol, etc.) in order to generate a mixed solution with organic solvent or water-organic solvent, the slurry of the yeast cell wall fraction aggregates, the concentration of the solid content of the fraction increases and the vapor pressure decreases and water component can easily evaporate. Therefore, it could be dried in a short time without heating at a high temperature (100° C. or more), which is required when water-dispersed slurry was directly heated and heating history can be decreased.

[Use of the Decolorized Yeast Cell Wall Fraction]

(Type of Usage of the Decolorized Yeast Cell Wall Fraction)

The decolorized yeast cell wall fraction of the present invention is generally in a form of slurry, but it can be also used in a dried form. For example, water dispersed moiety of the decolorized yeast cell wall fraction can be powdered by a common drying-method such as spray-dry method, freeze-dry method to obtain powder or dried material of the decolorized yeast cell wall fraction.

(Pharmaceutical or Food Additives Containing the Decolorized Yeast Cell Wall Fraction as Primary Component)

The decolorized yeast cell wall fraction of the present invention has a white color, no odor and shows a strong binding ability in a dried condition, but as it disintegrates in water, it could be used in a wide range for pharmaceutical or food additives. For example, a combination with coating agent, capsule material, adsorbent, stabilizer, moisturizing agent such as cream, granulation aids, suspending agents, fluidization agent, binder, new excipient having forming ability and disintegration ability of granulation by being mixed with crystal cellulose and dried, and other coating agents can be exemplified.

It will be explained in detail in the following.

(Physical Property of the Decolorized Yeast Cell Wall Fraction as a Coating Agent)

The coating agents containing the decolorized yeast cell wall fraction of the present invention as primary component, have excellent properties allowing them to be used as bitterness masking agents or enteric coating agents which have a nonsticky finish despite their viscosity, resulting in coated particles and/or granules that do not aggregate, and which are capable of controlling the time at which dissolution begins, in comparison with conventional edible coating agents. Moreover, the coating film has extremely low oxygen or other gas permeability and moisture permeability, and is extremely excellent among existing edible films, making it preferable as whisker inhibitor or odor masking agent. When the gas permeability is high, the wrapped drugs could degrade, which is not preferable.

Furthermore, the decolorized yeast cell wall fraction of the present invention is preferable as no delay of disintegration occurs even when the coating level is increased. Conventional coating is not preferable because disintegration property worsens after coating.

When the decolorized yeast cell wall fraction of the present invention is used as a coating agent, the solid concentration is preferably 0.1-30%, and more preferably 1-10%. It is not preferable that the solid concentration reaches 30% or more, because it arises a problem: viscosity of the coating liquid increases and as a result, spray mists cannot keep their small size and aggregation occurs.

(Substances Coated with the Decolorized Yeast Cell Wall Fraction)

Any substance that is a solid at ordinary temperature can be used as the substance coated with the coating agent of the present invention. Examples include food products, food product materials, enzymes, microorganisms, pharmaceuticals, seeds, agrochemicals, fertilizers, flavors and pigments. Specific examples of the aforementioned food products and food product materials include starch food products, tableted food products, Western style confectioneries (candies, sweets, chocolate, chewing gum, etc.), Japanese style confectionaries (such as crackers:senbei), baked confectionaries (such as sponge cakes, cookies, and crackers), gummy candies, fried snacks (such as chips of potatoes or the like, snacks, and the like), various sauces, soy sauce, miso sauce, mayonnaise, or dressings in the form of powders or solids, various beverages (such as fruit juices, nectars, rolling beverages, sports beverages, teas, coffee, cocoa, soups, and alcoholic beverages) in the form of powders or solids, various powder extracts (meats such as beef, pork, or chicken, seafood such as shrimps, prawns scallops, corbicula, kelp and any marine products, vegetables and fruits, plants, yeast, etc.), oils and flavoring (vanilla, citrus, bonito, etc.) in the form of powders or solids, powdered spices and herbs (red pepper, black pepper, Japanese sansho pepper, yuzu citron, basil, and the like), powdered beverages (such as instant coffee, instant tea, instant milk, instant soups and miso soups, etc.), various dairy products (such as cheese), various nutrient and nutritional supplement food materials (such as vitamins A, B, C, D, and E, edible microorganism of Bifidobacterium, Lactic acid bacteria, butyric acid bacteria and other useful bacteria, chlorella, calcium and magnesium minerals, propolis, and the like), sprinkles, flakes, toppings (such as croutons),processed soy (such as tofu and bean curd dregs) in the form of solids, fresh and processed foods (such as curry and stews) in the form of solids and frozen foods (plain and coatings), and various processed food products.

The coating agents of the present invention are suitable for use when the substances to be wrapped are in granulated form, such as microparticles, granules, or tablets, or when the substance to be wrapped itself is in a form resembling granules, such as seeds. Moreover, by coating such substances to be wrapped with the coating agent of the present invention, the coated material of the present invention can be obtained. Further, when the coating agent of the present invention is used to produce a film without coating the substance to be wrapped, the coating film of the present invention, which has an extremely low oxygen permeation coefficient or moisture permeation coefficient can be obtained.

(Plasticizers and Additives for Enhancing Formation, to Add to the Coating Agents Containing the Decolorized Yeast Cell Wall Fraction as Primary Component)

The use of the decolorized yeast cell wall fraction of the present invention by itself has an excellent effect, but it is preferable to add plasticizers. Examples of the plasticizers include in the field of food products: glycerin sorbitol, amino acids, organic acids, monoglycerides, diglycerides, triglycerides, and MCT (middle chain triacyl glycerol)-based oils. In the field of pharmaceutical, triacetin, triethyl citrate, acetylated monoglycerides, and any other plasticizer acceptable as pharmaceutical additives can be exemplified. Further, in addition to the plasticizers, or in place of the plasticizers, the following additives can be added.

As additives, examples include: viscosity-increasing polysaccharides (arabic gum, pullulan, karaginan, etc.), polysaccharides-degrading substances (degrading substances such as mannan, curdlan, xylan, cellulose, etc.), oligosaccharides (trehalose, sucrose, palatinose, raffinose, oligosaccharides, etc), sugar alcohols (mannitol, sorbitol, maltitol, Palatinit, erythritol, arabitol, xylitol, glucitol, glactitol, ribitol, etc.), dietary fibers (pine fibers, etc.), stevia, cyclo dextrin, gelling agents (agar, gelatine, gellan gum, curdlan, etc.), arginine hydrochloride, ferrous sulfate, phosphate (sodium phosphate, potassium phosphate), aleurone hydrolysate, adipic acid dioctyl, aluminium silicate, triethyl citrate, gliceric fatty acid ester, oils (sesame oil, liquid paraffin, corn oil, soy oil, castor oil, peanut oil, mixture of cotton seed oil/soy oil, etc.), mixture of dimethyl polysiloxane/disilicone, sucrose fatty acid ester, dipropylene glycol, propylene carbonate, middle-chain fatty acid triglyceride, triacetin, phytosterol, dimethyl phthalate, diethyl phthalate, dioctyl phthalate, dibutyl phthalate, butyl phthalyl butyl glycolate, propylene glycol, polyoxyethylene (105) polyoxy-propylene (5) glycol, polysorbate 80, polyvinyl alcohol, polyvinyl pyrrolidone, polypropylene glycol 2000, macrogol, isopropyl myristate, glycerin monostearate, linoleate isopropyl.

Furthermore, any of the above-mentioned plasticizers and additives can be added to the decolorized yeast cell wall fraction of the present invention with the following combination: one or more of either plasticizers or additives; one plasticizer and one additive, or two or more plasticizers and two or more additives; one plasticizer and two or more additives, or two or more plasticizers and one additive.

(Oxygen-Barrier Property Enhancer to be Added to a Coating Agent Made of Decolorized Yeast Cell Wall Fraction)

Compared to using the decolorized yeast cell wall fraction by itself, it is preferable to add additives (oxygen-barrier property enhancer) to enhance oxygen-barrier property. As for oxygen-barrier property enhancers to be added, saccharides having short chains such as monosaccharides (e.g. sucrose, glucose, mannose, etc.), or oligosaccharides (e.g. maltose, trehalose, fructose, arabinose, nigerooligosaccharide, lactose, D-glucono-1,5-lactone, etc.); low-hygroscopic amino acids (e.g. arginine hydrochloride etc.); inorganic salts forming multihydrates (e.g. ferrous sulfate, sodium dihydrogen phosphate, etc.); low-hygroscopic sugar alcohols (e.g. mannitol, Palatinit, maltitol, etc.); vitamins (e.g. vitamin C etc.); existing coating agents (PVA (polyvinyl alcohol), Eudragit L30-D55; hydroxy propyl methyl cellulose (HPMC TC-5), etc.); viscosity-increasing polysaccharides (e.g. arabic gum, etc.); gelling agent (gelatin, etc.) can be exemplified. There is no specific limitation for oxygen-barrier property enhancers, however when it is used for foods or pharmaceutical dosage forms, agents composed of edible materials are preferable. Further, microparticles such as titanium oxide, zinc oxide, alminium oxide, talc, maica, montmorillonite, bentonite (dispersed materials at nano levels are preferable) can be added as for inorganic materials.

These oxygen-barrier property enhancers can be used independently or by combining two or more kinds appropriately, and a combination of the above-mentioned plasticizer and additives for enhancing the film producing property is preferable (oxygen-barrier property enhancer+plasticizer, or oxygen-barrier property enhancer+additives other than oxygen-barrier property enhancer, or oxygen-barrier property enhancer+plasticizer+additives other than oxygen-barrier property enhancer).

(Preparation of Solid Dosage Forms Using Inhibitor of Volatilization or Sublimation)

When preparing solid dosage forms using inhibitor of volatilization or sublimation, containing decolorized yeast cell wall fraction of the present invention as primary component, there is no specific limitation as long as volatile or sublimate substances are basically coated with the inhibitor of volatilization or sublimation of the present invention to form a blockage with the outer side, and usually a proper means of solid dosage forms used in this field such as mixture and coating are used. To prepare solid dosage forms such as drugs by using the inhibitor of volatilization or sublimation of the present invention, for example, the solid dosage forms such as granules and tablets can be molded by compounding the inhibitor of volatilization or sublimation of the present invention with various excipients, additives, lubricants and the like. The resultants are granulated by wet or dried granulation methods or granulation methods such as direct compression method. Further, when making dosage forms coated by the inhibitor of volatilization or sublimation of the present invention, granules or tablets, which are granulated after compounding excipients or other compounding agents with effective components, are possible to be made into dosage forms by coating whisker-inhibitor with a commonly used coating method.

(Physical Properties of Dosage Forms by Coating the Inhibitor of Volatilization or Sublimation of the Present Invention)

The dosage forms by coating with the use of the inhibitor of volatilization or sublimation comprising the decolorized yeast cell wall fraction of the present invention is particularly effective for preventing whisker generation.

The coating using the inhibitor of volatilization or sublimation of the present invention has excellent properties allowing them to be used as bitterness masking agents or enteric coating agents which, compared to conventional edible coating agents, have a nonsticky finish despite their viscosity, resulting in coated particles and/or granules that do not aggregate, and which are capable of controlling the time at which dissolution begins. Coating layers (films) comprising the coating agents of the present invention have an extremely low oxygen or other gas permeability and moisture permeability, and are extremely excellent among existing edible films, making them suitable for use in a wide range of fields, such as food products, pharmaceutical, feed, agrochemicals, and the like.

Moreover, as the inhibitor of whisker generation of the present invention, that is the coating agent itself, has no specific medicinal effects, it does not effect the intended medicinal effect and does not impair versatility, which is different from when compounding components having medicinal effects such as antacids. Furthermore, it is known that the disintegration property of the conventional coating worsens when coated while the present invention has no influence on the disintegration property and no deterioration of dosage forms due to mutual reaction with the internal material is observed.

(Substances to be Wrapped by the Solid Dosage Form Inhibiting Volatilization and Sublimation)

As for volatile or sublimate substances in the solid dosage form having as object to inhibit volatilization or sublimation in the present invention, various substances being volatile or sublimate at ordinary temperature contained in solid dosage form of pharmaceuticals, foods, food materials, food additives, agrichemicals or flavor can be estimated. Particularly, as for object substances for inhibiting whisker generation and the like, the following can be exemplified.

In other words, as for sublimate materials at ordinary temperature, examples include: caffeine such as caffeine (1 hydrate), anhydrous caffeine, caffeine citrate, sodium benzoate caffeine; salicylic acid, aspirin, acetaminophen, ethenzamide, chlorphenira mine maleate, tipepidine hibenzate, noscapine, carbetapentane citrate, potassium guaiacol sulfonate; extracts such as ephedra herb, cinnamon bark, Pheretima asiatica, ginseng, glycyrrhiza, oriental bezoar as herbal medicine; extracts such as Kakkonto, Shosaikoto, Shoseiryuto, Saikokeishito as Chinese medicine; menthols such as l-menthol, d-menthol, dl-menthol; benzoates such as ethyl benzoate, phenyl benzoate, propyl benzoate, benzyl benzoate, methyl benzoate, sodium benzoate.

(Coating of Solid Dosage Form with the Inhibitor of Volatilization or Sublimation Using the Decolorized Yeast Cell Wall Fraction)

The coating using the inhibitor of volatilization or sublimation of the present invention intended to prevent generation of whisker can be conducted as follows: granulations with suitable diameter, such as microparticles, granules or tablets are prepared with the use of the aforementioned substances to be wrapped of the present invention alone or in combination; the inhibitor of volatilization or sublimation of the present invention is suspended in water or a mixture of water and solvent; and with the resulting suspension, the granulations can be coated.

(Coating Process Using the Decolorized Yeast Cell Wall Fraction)

By the coating using the coating agent of the present invention, substances suspended in water or a mixture of water and solvent can be coated. Specifically, a coating device such as the Doria Coater (by Powrex Co., Ltd), for example, can be used to spray coat the substance to be wrapped with a suspension of the coating agent of the present invention, although any common coating method or device can be used.

(Drying Temperature and Amount in the Coating Process Using the Decolorized Yeast Cell Wall Fraction)

The drying temperature during the coating process, that is, the drying temperature after the substance to be wrapped has been coated with the suspension of the coating agent of the present invention, is not particularly limited, although it is preferable that the substance should ordinarily be dried at a temperature of between 60-90° C. The drying temperature can be set according to the temperature stability of the substance to be wrapped as well. It is not preferable to dry at a temperature of 90° C. or more, as the film property will worsen. Moreover, by further drying after the completion of the coating, the film stability will be enhanced and the dissolution of the coated materials can be controlled stably. It is preferable to determine the amount of coating agent properly according to the amount of the substance to be wrapped, the intended application, and so on.

(Substances to Combine with the Decolorized Yeast Cell Wall Fraction)

Moreover, when the decolorized yeast cell wall fractions of the present invention are used for pharmaceuticals or foods as above mentioned, it is preferable to use by combining with the following substances. Specific examples include stabilizing agents (e.g. trehalose, mannitol, fumaric acid, etc.), excipients (e.g. micro crystal cellulose, corn starch, potato starch, rice starch, lactose, powder sugar, etc.), binders (e.g. hydroxypropyl methylcellulose, polyvinyl alcohol, polyvinylpyrrolidone, pullulan, etc.), film coating agents (e.g. hydroxypropyl cellulose, hydroxypropyl methylcellulose, hydroxypropyl cellulose phthalate, hydroxypropyl methycellulose acetate succinate, carboxy methyethyl cellulose, ethyl cellulose, ethyl celluloseaqueous dispersion, aminoalkyl methacrylate copolymer E, methacrylate copolymer L, methacrylate copolymer S, methacrylate copolymer LD, aminoalkyl methacrylate copolymer RS, etc.), surfactants (e.g. sucrose esters of fatty acids, polyoxyethylene polyoxypropylene glycol, polysorbate, sodium lauryl sulfate, sugar, etc.), disintegration agents (e.g. low substituted level hydroxypropyl cellulose, carmellose calcium, cross carmellose sodium, partly pregelatinized starch, etc.), inorganic substances (e.g. talc, magnesium sterate, light anhydrous silicic acid, synthetic aluminum silicate, titanium oxide, etc.), plasticizers (e.g. arabic gum, pullulan, karaginan, etc.), polysaccharide-degrading substances (e.g. degrading substances such as mannan, curdlan, xylan, cellulose), oligosaccharides (e.g. sucrose, palatinose, raffinose, oligosaccharides, etc.), sugar alcohols (e.g. sorbitol, maltitol, Palatinit, erythritol, arabitol, xylitol, glucitol, glactitol, ribitol, etc.), dietary fibers (e.g. pine fiber, etc.), stevia, cyclo dextrin, gelling agents (agar, gelatin, gellan gum, curdlan, etc.), amino acids (e.g. arginine hydrochloride, etc.), inorganic salts forming multihydrates (e.g. ferrous sulfate, etc.), phosphate (e.g. sodium phosphate, potassium hydrochloride, sodium dihydrogen phophate, etc.), starch hydrolysate, dioctyl adipate, aluminium silicate, triethyl citrate, gliceric fatty acid ester, oils (e.g. sesame oil, liquid paraffin, corn oil, soy oil, castor oil, peanut oil, mixture of cotton seed oil/soy oil, etc.), mixture of dimethyl polyxane/disilicone, dipropylene glycol, propylene carbonate, middle-chain fatty acid triglyceride, triacetin, fit sterol, dimethyl phthalate, diethyl phthalate, dioctyl phthalate, dibutyl phthalate, butyl phtalyl butyl glycolate, propylene glycol, polyoxyethylene (105) polyoxy prolylene (5) glycol, polysorbate 80, polypropylene glycol 2000, macrogol, isopropyl myristate, glycerin monostearate, linoleate isopropyl, etc.). These are typical examples and any substances described in Japanese Pharmacopoeia, Fourteenth Edition or in Japanese Pharmaceutical Excipients Directory, published in 1996 can be used in combination.

Moreover, when using the present invention as foods/health foods, when using for the aforementioned purpose, it can be used in combination with those listed in the food additives list.

The present invention will be described in further detail below with reference to the examples, but is not limited to these.

METHOD FOR MEASURING PHYSICAL PROPERTIES IN THE EXAMPLES

Methods for measuring each physical property in the examples and comparative examples other than mentioned in the above, are as follows. The amount of the decolorized yeast cell wall fraction given in the examples is actual weight (dry weight).

Various properties at the point when tablets are formed by using the present invention are measured as follows.

(Disintegration Property of Tablets)

According to the disintegration test described in the Japanese Pharmacopoeia, Fourteenth Edition, the test was performed by using disintegration test device NT-40HS (Toyama Sangyo). Pure water of 37° C. was used as test solution and the results are shown by the average disintegration time of six tablets.

(Tablet Hardness)

The average hardness of 10 tablets was obtained by using 6D-type Schleuniger hardness tester (Freund).

(Sensory Evaluation of Odor)

20 tablets, which were 10%-coated based on tablet weight, were tightly sealed in a glass container. After resting them overnight at room temperature, three panelists evaluated the odor of drugs at the time of opening. For the tablets which three panelists answered that there was no odor of drugs, the odor masking was determined to be good, and for those which they answered that there was odor of drugs, the odor masking was determined to be not made.

(Washing Method with Water by Centrifugation)

The reaction solution was centrifuged by using a centrifugal separator (Hitachi: himac CR7) at a condition of 4200 rpm/10 min to obtain precipitated fractions. Water, approximately 3-fold by weight of the precipitated fraction was added to re-disperse, the mixture was centrifuged to obtain precipitated fractions. Herein after, this process is defined to be 1 time of water-washing by centrifugation. When the above-mentioned process from adding water to centrifugation is repeated for N times, it is described as N times of water-washing by centrifugation, and this expression is used hereinafter. Additionally, this expression is used not only for the centrifugal device for the aforementioned Batch style treatment, but also for the continuous discharge-type centrifugal separator.

Example 1

According to the method described in U.S. Pat. No. 3,349,677, the internal cell components are dissolved with protease (by NOVO, with the use of Neutrase, Alkalase, reacted at 45-60° C., at pH 7.5 for 15 hours), the yeast cell wall fractions (liquid YI:45) wherein the internal soluble cell components are removed by centrifugation (4200 rpm, 10 min) are treated for 10 min with 5% yeast cell wall fraction concentration, under the condition of 0.5 N hydrochloric acid at 80° C., then washed with water after removing the acid-soluble internal cell components by centrifugation, to produce acid-treated yeast cell wall fractions. The acid-treated yeast cell wall fractions (liquid YI:49) were adjusted to a concentration of 5% yeast cell wall fraction concentration, the decolorization treatment of the acid-treated yeast cell wall fraction of 5% concentration was performed by reacting for 3 hours at a constant pH, under a condition of 1.5% hydrogen peroxide concentration, pH 10, a temperature of 60° C. Following the reaction, the resultant was centrifuged (4200 rpm, 10 min) and washed sufficiently with water. The washed substance was reacted again with the above reaction condition for 15 hours, centrifuged (4200 rpm, 10 min) and washed with water.

The liquid YI of the washed substance (Example Item 1) was 12, with film property (11 ml/m$^2$·d·MPa), with film disintegration property (28 min).

Example 2

Centrifuged and separated sludge of Example 1 was dispersed in 99.5% ethanol of 3-fold amount, stirred for 30 min, centrifuged to remove ethanol of the supernatant, and further centrifuged to wash with water sufficiently. The liquid YI of the washed substance (Example Item 2) was 12, with film property (13 ml/m$^2$·d·MPa), with film disintegration property (29 min).

Example 3

10000 ppm ozone gas was injected to decolorize into 600 g slurry of 5% concentration-acid-treated yeast cell wall fractions described in Example 1, at a rate of 3 g/hr for 15 hours. In case the item is left being only washed after the ozone treatment, a color reversion phenomenon will occur and the decolorized item whitened by the treatment will be colored again to burned umber. Therefore, pH was adjusted to 11 with sodium hydroxide, dissolved, centrifuged (4200 rpm, 10 min) to wash with water and then subjected to the same ozone injecting treatment as above for 2 hours. The remaining ozone of the ozone-treated substances are reduced and degraded with sodium sulfite, adjusted to pH11 with sodium hydroxide, centrifuged (4200 rpm, 10 min), washed further to remove substances generating color reversion phenomenon. The liquid YI of the washed substance (Example Item 3) was 0, with film property (10 ml/m$^2$·d·MPa), without film disintegrating property (over 60 min).

Example 4

600 g slurry of 5% concentration-acid-treated yeast cell wall fractions described in Example 1 were reacted with 200 g sodium hypochlorite with 12% of effective chlorine concentration at pH1.2. After 2 hours of reaction, the resultant was centrifuged (4200 rpm, 10 min) and washed with water. The liquid YI of the washed substance (Example Item 4) was 11, with film property (11 ml/m$^2$·d·MPa), with film disintegration property (30 min)

Example 5

The yeast cell wall fractions were adjusted to 10% slurry, treated 12 times with a high pressure homogenizer at 50 MPa, and the crashed yeast cell wall fractions were treated with 0.1 N hydrochloric acid at 80° C. for 10 min, washed by centrifuging (4200 rpm, 10 min). 1% sodium hypochlorite solution (effective chlorine concentration 12%) was added to the acid-treated yeast cell wall fraction thus obtained by washing and adjusted to 5% slurry, and the fractions were decolorized under acid condition with hydrochloric acid (pH 1-2). The decolorized item (Example Item 5) was significantly whitened. The liquid YI of the Example Item 5 was 1, with film property (13 ml/m$^2$·d·MPa), without film disintegration property (over 60 min).

Example 6

1000 g slurry of 5% concentration-acid-treated yeast cell wall fractions described in Example 1, were reacted for 3 hours at a constant pH under a condition of 3% hydrogen peroxide concentration, pH 10, temperature of 60° C. After the reaction, the resultant was washed with water sufficiently by centrifugation (4200 rpm, 10 min). The slurry was adjusted to pH 7-7.5 with 4N hydrochloric acid, to which 0.05-0.1% of catalase (Nagase Chemtex, Leonet F Plus) was added, the resultant was stirred for 30 min to degrade the remaining hydrogen peroxide, water-washed by centrifugation twice to obtain precipitated fractions. The precipitated fractions were adjusted to pH 4 with 4 N hydrochloric acid, ozone was injected to 1.5 L of the 3% slurry under the condition of pressure 0.1 MPa, liquid temperature 10° C. and the ozone treatment was performed for 1 hour. An oxygen/ozone-mixture gas generated with a commercial electric discharged-type ozonizer by supplying oxygen from an oxygen cylinder was used as ozone gas. The gas was injected under the condition of pressure 0.11 MPa, flow rate 2 L/min, ozone concentration 4.5% (w/w), and the ozone gas became in form of fine bubbles and a gas-liquid reaction was conducted. The remaining ozone of the ozone-treated substance was reduced and degraded with sodium sulfite, adjusted with sodium hydroxide to pH 11, centrifuged (4200 rpm, 10 min), washed with water sufficiently to obtain precipitated fractions. The precipitated fractions was dissolved in equal amount of 99.5% ethanol, stirred for 30 min, ethanol of the supernatant was removed by centrifugation, and the resultant was further washed with water by centrifugation to obtain Example Item 6. The liquid YI of the Example Item 6 was 0, with film property (16 ml/m$^2$·d·MPa), without film disintegration property (over 60 min).

Example 7

The decolorization treatment of the 5% concentration-acid-treated yeast cell wall fractions obtained at hydrogen peroxide concentration 3.0%, pH 10, temperature 60° C. in the same manner as Example 1 was performed at a constant pH for 3 hours, and washed sufficiently with water by centrifugation (4200 rpm, 10 min) after the reaction. The washed substance was reacted for 15 hours with the above-mentioned reaction condition, water-washed by centrifugation (4200 rpm, 10 min) The obtained resultant was named as Example Item 7.

The liquid YI of the Example Item was 1, with film property (10 ml/m$^2$·d·MPa), with film disintegration property (28 min)

Example 8

Ozone was injected to 1 L of 5% slurry of the acid-treated yeast cell wall fraction described in Example 1 adjusted to pH 4 with 4 N hydrochloric acid, under the condition of pressure 0.1 MPa, liquid temperature 10° C, and the ozone treatment was performed for 1 hour. An oxygen/ozone mixture generated with a commercial electric discharge-type ozonizer by supplying oxygen from an oxygen cylinder was used as ozone gas. The gas was injected under the condition of pressure 0.11 MPa, flow rate 2 L/min, ozone concentration 4.5% (w/w), and the ozone gas became in form of fine bubbles and a gas-liquid reaction was conducted. After the completion of ozone treatment, the resultant was adjusted to pH 11 with 25% sodium hydroxide solution, water-washed by centrifugation twice under the condition of 4200 rpm, 10 min. The obtained precipitated fractions were adjusted to pH 3.8 and the adjusted fractions were named as Example Item 8. The liquid YI of Example Item 8 was 9, with film property (10 ml/m$^2$·d·MPa), without film disintegration property (over 60 min).

Example 9

Substances treated in the same were adjusted to a slurry of 2.5% dry matter concentration, 2% hydrogen peroxide concentration, and pH 10 with 25% sodium hydroxide, and reacted for 5 hours at 60° C. After the reaction, centrifugation was performed at 4200 rpm for 10 min, the centrifuged precipitates were diluted with water to obtain slurry with dry matter concentration of about 3%. The slurry was adjusted to pH 7-7.5 with 4 N hydrochloric acid, to which 0.05-0.1% of catalase (Nagase Chemtex: REYONET F Plus) was added, and stirred for 30 min. The remained hydrogen peroxide was degraded and removed, water-washed by centrifugation twice, to obtain precipitated fractions. Weight of ethanol equal to that of the obtained precipitated fractions was added to the precipitated fractions, the resultant was dispersed by stirring, and made in a slurry form, stirred for 30 min and centrifuged. After this treatment of ethanol-washing by centrifugation was performed 3 times, water-washed by centrifugation was performed twice. The obtained precipitated fractions were adjusted to pH 3.8, and named as Example Item 9. The liquid YI of the Example Item 9 was 0, with film property (10 ml/m$^2$·d·MPa), with film disintegration property (7 min).

Example 10

Substances treated in the same manner as Example 8 (ozone treatment followed by alkaline treatment) was adjusted to a slurry of 2.5% dry matter concentration, 2% hydrogen peroxide concentration, and pH10 with 25% sodium hydroxide, and reacted for 2 hours at 60° C. After the reaction, centrifugation was performed at 4200 rpm for 10 min, the centrifugates were diluted with water to obtain a slurry with dry matter concentration of about 3%. The slurry was adjusted to pH 7-7.5 with 4 N hydrochloric acid, to which 0.05-0.1% of catalase (Nagase Chemtex: REYONET F Plus) was added, and stirred for 30 min. The remained hydrogen peroxide was degraded and removed, water-washed by centrifugation twice, to obtain precipitated fractions. Weight of ethanol equal to that of the obtained precipitated fractions was added to the precipitated fractions, the resultant was dispersed by stirring, and made in a slurry form, stirred for 30 min, then water-washing by centrifugation was performed twice, the obtained fractions were adjusted to pH 3.8, and named as Example Item 10. The liquid YI of the Example Item 10 was 0, with film property (10 ml/m$^2$·d·MPa), with film disintegration property (14 min).

Example 11

According to the method described in U.S. Pat. No. 3,349,677, brewer's viable yeast slurry in a viable condition obtained as a by-product material of the brewing process was centrifuged (4200 rpm, 10 min), and the obtained yeast was suspended so that the solid content became 10 wt %. The yeast was treated with a 100 MPa-homogenizer, and the internal cell components were dissolved with protease (NOVO, reacted by using Neutrase, Alcalase, at 45-60° C., at pH 7.5 for 15 hours). The slurry was centrifuged (4200 rpm, 10 min) to remove internal soluble cell components, and the obtained cell residue was washed with water to generate yeast cell wall fractions (YCW). Slurry of the YCW adjusted to 5% dried-weight concentration, 1% hydrogen peroxide concentration, and to pH 10 with 25% sodium hydroxide concentration, and was reacted at 60° C. for 2.5 hours. Then, an amount equivalent to 1% hydrogen peroxide was added again, pH was adjusted again to 10 with 25% sodium hydroxide and the resultant was reacted at 60° C. for 2.5 hours. After the reaction, centrifugation was performed at 4200 rpm for 10 min, the centrifuged precipitates were diluted with water, to generate a slurry with dry material concentration of about 3%. The slurry was adjusted to pH 7-7.5 with 4N hydrochloric acid, to which 0.5% catalase (Nagase Chemtex: REYONET F Plus) was added, stirred for 30 min to degrade and removed the remaining hydrogen peroxide, and water-washing by centrifugation was performed twice. The obtained precipitated fractions were adjusted to pH 3.8, and the fraction was named as Example item 11. The liquid YI of Example Item 11 was 13, with film property (10 ml/m$^2$·d·MPa), with film disintegration property (14 min).

Example 12

Ozone was injected to 1 L of 5% slurry of YCW adjusted to pH4 with 4N hydrochloric acid, under the condition of pressure 0.1 MPa, liquid temperature 10° C., and the ozone treatment was performed for 1 hour. An oxygen/ozone mixture gas generated with a commercial electric discharged-type ozonizer by supplying oxygen from an oxygen cylinder was used as ozone gas. The gas was injected to the YCW slurry under the condition of pressure 0.11 MPa, flow rate 2 L/min, ozone concentration 4.5% (w/w), and the ozone gas became in form of fine bubbles and a gas-liquid reaction was conducted. After the ozone treatment, the resultant was adjusted to pH11 with 25% sodium hydroxide solution, water-washing by centrifugation was performed twice under the condition of 4200 rpm, 10 min. The obtained precipitated fractions were adjusted to pH 3.8 and the adjusted fractions were named as Example Item 12. The liquid YI of the Example Item 12 was 6, with film property (10 ml/m$^2$·d·MPa), without film disintegration property (over 60 min).

Example 13

Ozone was injected to 1 L of 2.5% slurry of Example 12, under the condition of pressure 0.1 MPa, liquid temperature 10° C., and the ozone treatment was performed for 0.5 hour. An oxygen/ozone mixture gas generated with a commercial electric discharged-type ozonizer by supplying oxygen from an oxygen cylinder was used as ozone gas. The gas was injected to the YCW slurry under the condition of pressure of 0.11 MPa, flow rate 2 L/min, ozone concentration 7.2% (w/w), and the ozone gas became in form of fine bubbles and a gas-liquid reaction was conducted. After the ozone treatment, the resultant was adjusted to pH 11 with 25% sodium hydroxide solution, water-washing by centrifugation was performed twice under the condition of 4200 rpm, 10 min. The obtained precipitated fractions were adjusted to pH 3.8 and the adjusted fractions were named as Example Item 13. The liquid YI of the Example item 13 was 0, with film property (10 ml/m$^2$·d·MPa), without film disintegration property (over 60 min).

Example 14

Amount of ethanol equal to that of the precipitated fractions before adjusted to the final pH 3.8 of Example 13, was added to the precipitated fractions, stirred to obtain a form of slurry and stirred for 30 min. The precipitated fractions obtained by performing water-washing by centrifugation twice, were adjusted to pH 3.8. The obtained fractions were named as Example Item 14. The liquid YI of the Example Item 14 was 0, with film property (10ml/m$^2$·d·MPa), without film disintegration property (over 60 min).

Example 15

Example item 12 was adjusted to slurry with 2.5% dry material concentration, 1% hydrogen peroxide concentration, and pH 10 with 25% sodium hydroxide, and reacted at 60° C. for 2 hours. After the reaction, centrifugation was performed at 4200 rpm for 10 min, the centrifuged precipitates were diluted with water to obtain slurry of dry material concentration of about 3%. The slurry was adjusted to pH 7-7.5 with 4 N hydrochloric acid, to which 0.05-0.1% catalase (Nagase Chemtex: REYONET F Plus) was added, stirred for 30 min. The remaining hydrogen peroxide was degraded and removed, water-washed by centrifugation twice. The obtained precipitated fractions were adjusted to pH 3.8, and named as Example Item 15. The liquid YI of the Example Item 15 was 0, with film property (10 ml/m$^2$·d·MPa), with film disintegration property (19 min).

Example 16

Amount of ethanol equal to that of the precipitated fractions before adjusted to the final pH 3.8 of Example 15, was added to the precipitated fractions, stirred to obtain a form of slurry, and stirred for 30 min. The precipitated fractions obtained by performing water-washing by centrifugation twice, were adjusted to pH 3.8. The obtained fractions were named as Example item 16. The liquid YI of the Example Item 16 was 0, with film property (10 ml/m$^2$·d·MPa), with film disintegration property (9 min).

Comparative Example 1

10 g of dried yeast extract residues were suspended in 500 g NaOH solution of 0.5 N concentration. 100 g of 2% hydrogen peroxide were mixed, and after 120 min of reflux boiling, the precipitated fractions were washed with water by centrifugation, and then named as Comparative Example Item 1. The liquid YI of the Comparative Example Item 1 was 7, without film property (more than 250 ml/m$^2$·d·MPa). As no continuous film was formed, the film disintegration property was impossible to measure.

Comparative Example 2

20 g of dried yeast extract residues were suspended in 1000 g NaOH solution of 0.5 N concentration, and reflux-boiled for 120 min. The resultant was washed with water by centrifugation, and the precipitated fractions were suspended into 1000 g of 0.5 N hydrochloric acid solution, reflux-boiled for 120 min. The precipitated fractions washed further with water by centrifugation (3000 rpm, 20 min) were named as Comparative Example Item 2. The liquid YI of the Comparative Example Item 2 was 30, without film property (more than 250 ml/m$^2$·d·MPa). As no continuous film was formed, the film disintegration property was impossible to measure.

Comparative Example 3

Comparative Example Item 2 was reflux-boiled with 1000 g of 2% hydrogen peroxide solution, and the precipitated fractions water-washed by centrifugation (3000 rpm, 20min) were named as comparative Example Item 3. The liquid YI of the Comparative Example Item 3 was 7, without film property (more than 250 ml/m$^2$·d·MPa). As no continuous film was formed, the film disintegration property was impossible to measure.

Comparative Example 4

20 g of dried yeast extract residues were suspended in 1000 g NaOH solution of 0.5 N concentration, reflux-boiled for 120 min. The resultant was water-washed by centrifugation, and the precipitated fractions were suspended into 1000 g of 0.5 N hydrochloric acid solution, reflux-boiled for 120 min. 10000 ppm of ozone was injected for 1 hour to the precipitated fractions further washed with water with centrifugation (3000 rpm, 20 min), then the fractions were water-washed by centrifugation. 1000 mL of 99.5% ethanol was added, and ethanol was removed by centrifugation. Then, water was added and water-washing by centrifugation was performed. The precipitated fractions thus obtained were named as Comparative Example Item 4. The liquid YI of the Comparative Example Item 4 was 1, without film property (more than 250 ml/m$^2$·d·MPa) . As no continuous film was formed, the film disintegration property was impossible to measure.

Comparative Example 5

Brewer's yeast was autolysed, and the yeast cell wall fractions wherein the extract was removed by water-washing was adjusted to 5% of solid content concentration (weight ratio), to prepare 1 L of water dispersion. The resultant was adjusted to pH 8.5 with sodium bicarbonate, and stirred at ordinary temperature for 1 hour. The dispersion was centrifuged at 4200 rpm for 10 min, the precipitated fractions were suspended to 2.5% sodium hydroxide, and the resultant was adjusted to pH 12.5. The resultant was maintained at 65° C. in a hot-water bath, hydrogen peroxide of 30% concentration was added and the resultant was adjusted so that the total concentration become 1.5%. (hydrogen peroxide concentration), followed by a reaction of 15 hours. After the reaction, the resultant was adjusted to pH 7.0 with 12 N concentrated hydrochloric acid, the precipitated fractions were fractionated by centrifugation (4200 rpm, 10 min) so that the solid content concentration became 5%. The fractions adjusted to pH 5 by 4 N hydrochloric acid was named as Comparative Example Item 5. The liquid YI of the Comparative Example Item 5 was 36, without film property (more than 250 ml/m$^2$·d·MPa). As no continuous film was formed, the film disintegration property was impossible to measure.

Comparative Example 6

After autolysis of the brewer's yeast and removal of the extract, the acid-treated yeast cell wall fractions wherein acid treatment was performed according to the method of Example 1 was decolorized similarly as the method of Comparative Example 5. The obtained fractions were named Comparative Example Item 6. The liquid YI of the Comparative Example Item 6 was 31, without film property (more than 250 ml/m$^2$·d·MPa). As no continuous film was formed, the film disintegration property was impossible to measure.

Comparative Example 7

According to the preparation method of U.S. Pat. No. 3,349,677, YCW slurry of YCW dry material concentration 5% and 0.3 N hydrochloric acid concentration was maintained at 80° C. for 10 min, washed with water by centrifugation twice. The precipitated fractions were diluted in slurry of dry material concentration 5%, adjusted to pH 7.5, and then washed again with water by centrifugation twice. The resulted fractions were adjusted to pH 3.8 and named as Comparative Example Item 7. The liquid YI of the Comparative Example Item 7 was 49, with film property (5ml/m²·d·MPa), with film disintegration property (25 min).

Comparative Example 8

A slurry of 0.5 N sodium hydroxide concentration was prepared with YCW of dry material concentration of about 2%, and reflux-boiled for 120 min. After the reaction, slurry was recovered, and washed with water by centrifugation twice. The obtained fractions were named as Comparative Example Item 8. The liquid YI of the Comparative Example Item 8 was 49, without film property (more than 250 ml/m²·d·MPa). As no continuous film was formed, the film disintegration property was impossible to measure.

Comparative Example 9

A slurry of YCW dry material concentration of about 2.5%, 0.5 N sodium hydroxide concentration, and 2% hydrogen peroxide concentration was prepared, and reflux-boiled for 120 min. After the reaction, slurry was recovered, and washed with water by centrifugation twice. The obtained fractions were named as Comparative Example item 9.

Comparative Example 10

1000 g of slurry prepared from Comparative Example Item 8 by adjusting dry material concentration to about 2.5% was treated with ozone at ordinary temperature and ordinary pressure. As for the injection condition of ozone, an oxygen/ozone mixture gas generated with a commercial electric discharged-type ozonizer by supplying oxygen from an oxygen cylinder was used, the gas was injected to YCW slurry under the condition of pressure 0.11 MPa, flow rate 1 L/min, ozone concentration 10000 ppm, and the ozone gas became in form of fine bubbles and a gas-liquid reaction was conducted. After the reaction, the slurry was collected, and water-washing by centrifugation was performed twice. The obtained fractions were named as Comparative Example Item 10. The liquid YI of the Comparative Example Item 10 was 25, without film property (more than 250 ml/m²·d·MPa). As no continuous film was formed, the film disintegration property was impossible to measure.

Comparative Example 11

Weight of ethanol equal to that of the Comparative Example Item 10 was added, dispersed by stirring to obtain a form of slurry, stirred for 30 min and water-washing by centrifugation was performed twice. The obtained precipitated fractions were named as Comparative Example Item 11. The liquid YI of the Comparative Example Item 11 was 23, without film property (more than 250 ml/m²·d·MPa). As no continuous film was formed, the film disintegration property was impossible to measure.

Comparative Example 12

Comparative Example Item 8 was diluted to prepare 1000 g of slurry with 0.5 N hydrochloric acid concentration, and reflux—boiled for 120 min. After the reaction, slurry was recovered and water-washing by centrifugation was performed twice. The obtained precipitated fractions were adjusted to 1000 g slurry, and ozone treatment was performed at ordinary temperature and ordinary pressure. As for the injection condition of ozone, an oxygen/ozone mixture gas generated with a commercial electric discharged-type ozonizer by supplying oxygen from an oxygen cylinder was used, the gas was injected to YCW slurry under the condition of pressure 0.11 MPa, flow rate 1 L/min, ozone concentration 10000 ppm, and the ozone gas became in form of fine bubbles and a gas-liquid reaction was conducted. After the ozone treatment, slurry was recovered and water-washing by centrifugation was performed twice. Weight of ethanol equal to that of the obtained precipitated fractions were added to the precipitated fractions, the resultant was stirred to make a slurry form, then stirred for 30 min, and water-washing by centrifugation was performed twice. The obtained fractions were named as Comparative Example Item 12. The liquid YI of the Comparative Example Item 12 was 26, without film property (more than 250 ml/m²·d·MPa). As no continuous film was formed, the film disintegration property was impossible to measure.

Example 17

The solid content of Example Item 1 was dispersed into water so that trehalose as a plasticizer become 40 wt % of the solid content of the above-mentioned decolorized yeast cell wall fraction to prepare a coating solution. The solid content of each of the coating solutions is 5.8 wt % for Example Item 1. Moreover, as substances to be wrapped, after mixing crystal cellulose "Avicel" PH-301 (Asahi Kasei)/mannitol (TOWAKASEI Co., Ltd.)/L-cystein (Takeda Pharmaceutical Company Limited) at a weight ratio of 20/50/30, granules were produced by using L-HPC (Nippon Soda Co., Ltd.) as binding solution with multiplex MP-01 (Powrex), mixing the dried granules/magnesium stearate (Taihei Chemical Industrial Co., Ltd.) at a rate of 100/0.5, and Rotary tablet press machine (Kikusui Seisakusho Ltd.) was used to produce a tablet (uncoated tablet) with a diameter of 8 mm, weight of 200 mg, and hardness of 1 N. High Coater FREUND MODEL HCT-MINI (Freund) was used for coating, 400 g of uncoated tablets prepared beforehand was set, the coating solution was sprayed at 2.5 g/min under a condition of container-rotating speed 20 rpm, air temperature 80° C., exhaust gas temperature 35° C. and air pressure 0.1 MPa. Thus, the coating was performed so as the film amount become 10% based on tablet weight. Then, a drying treatment was performed overnight with a dryer at 60° C. to obtain a coated tablet. The coated tablet of the Example Item 1 was named as Tablet (a). As for coating operation, no aggregation between tablets was observed, and the surface of the tablet was coated uniformly and evenly on the surface. The YI of the tablet was 25, disintegration time was 460 seconds, odor masking was good and the tablet hardness was 2.1 N.

Example 18

A coating solution (concentration of solid content 7.3 wt %) was prepared in the same manner as Example 17, by using Example Item 7 and trehalose adjusted to 40 wt % of the solid content of Example Item 7. The same operation as Example 17 was performed, and coating tablet (b) was obtained. Coating was well performed. YI of the tablet was 11, disintegration time was 442 seconds, odor masking was good, and the tablet hardness was 2.1N.

Example 19

A coating solution (concentration of solid content 4.9 wt %) was prepared in the same manner as Example 17, by using Example Item 5 and trehalose adjusted to 40 wt % of the solid content of Example Item 5. The same operation as Example 17 was performed, and coating tablet (c) was obtained. Coating was well performed. YI of the tablet was 18, disintegration time was more than 1800 seconds, odor masking was good, and the tablet hardness was 2.1 N.

Example 20

A coating solution (concentration of solid content 7.0 wt %) was prepared in the same manner as Example 17, by using Example Item 9 and mannitol adjusted to 40 wt % of the solid content of Example Item 9. The same operation as Example 17 was performed, and coating tablet (A) was obtained. Coating was well performed. YI of the tablet was 7, disintegration time was 347 seconds, odor masking was good, and the tablet hardness was 3.3 N.

Example 21

A coating solution (concentration of solid content 8.0 wt %) was prepared in the same manner as Example 17, by using Example Item 16 and mannitol adjusted to 40 wt % of the solid content of Example Item 16. The same operation as Example 17 was performed, and coating tablet (B) was obtained. Coating was well performed. YI of the tablet was 7, disintegration time was 348 seconds, odor masking was good, and the tablet hardness was 3.3 N.

Comparative Example 13

A coating solution (concentration of solid content 11.1 wt %) was prepared in the same manner as Example 17, by using Comparative Example Item 7 and trehalose adjusted to 40 wt % of the acid-treated yeast cell wall fraction. The same operation as above was performed, and coating tablet (d) was obtained. Coating was well performed. YI of the tablet was 50, disintegration time was 434 seconds, odor masking was good, and the tablet hardness was 2.3 N.

Comparative Example 14

The same operation as Example 17 was performed to the coating solution of 5 wt % of HPMC (TC-5, Shin-Etsu Chemical) to obtain coated tablet (e). Coating was well performed as above. YI of the tablet was 12, disintegration time was 450 seconds, no odor masking, and the tablet hardness was 2.1 N.

Comparative Example 15

A coating solution (concentration of solid content 11.0 wt %) was prepared in the same manner as Example 17, by using Comparative Example Item 7 and mannitol adjusted to 40 wt % of the acid-treated yeast cell wall fraction. The same operation as Example 17 was performed, and coating tablet (C) was obtained. Coating was well performed. YI of the tablet was 55, disintegration time was 429 seconds, odor masking was good, and the tablet hardness was 2.1 N.

INDEPENDENT GAS-BARRIER PROPERTY OF THE COATING FILM OF THE COMPARATIVE EXAMPLES

Comparative Example 16

Oxygen permeability of Comparative Example Item 7 was 5 ml/$m^2$·d·MPa at a humidity of 60% RH.

Comparative Example 17

Oxygen permeability of HPMC:TC-5 (Shin-Etsu Chemical) was equal to or more than 172 ml/$m^2$·d·MPa.

Comparative Example 18

Oxygen permeability of EUDRAGIT L30-D55 (Higuchi Shokai) (mixed with weight ratio of EUDRAGIT/PEG2000/Tween 80=100/10/3.9) was 49 ml/$m^2$·d·MPa at a humidity of 60% RH.

Example 22

(Oxygen-Barrier Property Enhancer)

The whole solution was stirred and dispersed with a stirring bar so that the solid content of the Example item 7 becomes 5 wt % solution, and that the oxygen-barrier property enhancer becomes 10-80 wt % of the decolorized acid-treated yeast cell wall fractions to obtain an uniform solution.

The coating solution was casted using a baker applicator (Yoshimitsu Seiki), on a oriented-polypropylene film Senesi-POP (Daicel Chemical Industries), and dried in an oven at 60° C. for 45 min, to obtain a cast film with film thickness about 0.015 mm (overall film thickness 0.035 mm). OX-Train 100 of MOCON (Modern Controls) was used for the test system, the results obtained with measure conditions comprising temperature 20° C., humidity 60% or 85%, test area 5 $cm^2$, oxygen concentration 100% was calculated as oxygen permeability (mL/$m^2$·d·MPa), and shown in Tables 1 and 2. From Tables 1 and 2, it can be understood that when oxygen-barrier property enhancer is added to the decolorized acid-treated yeast cell wall fractions of the present invention, a good oxygen-barrier property can be obtained even under high humidity.

TABLE 1

| Samples (humidity 60% or less) | oxygen permeability level (mL/$m^2$ · d · MPa) |
|---|---|
| Example Item 7 | 10 |
| Example Item 7:mannitol = 10:2 | 3 |
| Example Item 7:mannitol = 10:4 | 3 |
| Example Item 7:mannitol = 10:6 | 5 |
| Example Item 7:mannitol = 10:8 | 4 |
| Example Item 7:trehalose = 10:4 | 2 |
| Example Item 7:PVA = 10:2 | 8 |
| Example Item 7:PVA = 10:4 | 2 |
| Example Item 7:sucrose = 10:4 | 3 |

TABLE 2

| Sample (humidity 85% or less) | oxygen permeability level (mL/$m^2$ · d · MPa) |
|---|---|
| Example Item 7 | 42 |
| Example Item 7:mannitol = 10:1 | 40 |
| Example Item 7:mannitol = 10:2 | 16 |
| Example Item 7:mannitol = 10:4 | 11 |
| Example Item 7:mannitol = 10:6 | 8 |
| Example Item 7:mannitol = 10:8 | 8 |
| Example Item 7:trehalose = 10:2 | 24 |
| Example Item 7:trehalose = 10:4 | 27 |
| Example Item 7:trehalose = 10:5 | 37 |
| Example Item 7:PVA = 10:2 | 34 |
| Example Item 7:PVA = 10:4 | 21 |
| Example Item 7:sucrose = 10:4 | 33 |
| Example Item 7:gum arabic = 10:4 | 32 |
| Example Item 7:gelatin = 10:4 | 32 |

Example 23

(Shapes of Yeast Cell Walls of Example Items and Existing Similar Articles (Comparative Examples))

Figure 2:
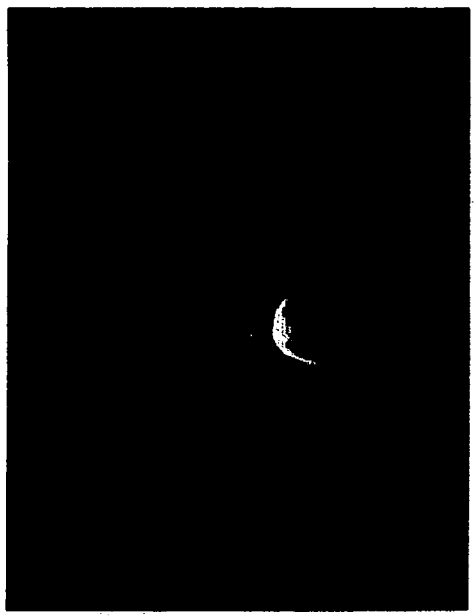
FIG. 2 is a set of pictures taken by scanning electron microscope (SEM) showing the difference of the cell wall shape retaining property between Example Items 1, 3 and Comparative Example Items 1, 3 of the present invention.
Figure 2:
Figure 2:
Figure 2:

The pictures of Example Items 1, 3 and Comparative Example Items 1, 3 were taken with Scanning Electron Microscope (SEM) (FIG. 2). The cell wall shape of Example Items (1 and 3) were fully remained (shape retained) (FIG. 2, A, B) while those of Comparative Example Items (1, 3) were not remained (FIG. 2. C, D).

Example 24

(Shape of Yeast Cell Walls of the Present Invention and Existing Similar Articles (Comparative Items) (Evaluation According to Particle Size Distribution))

In addition to Example Items 1 and 3, the distribution of particles was measured for Comparative Example Items 1, 3 and 4 by using a laser scanning particle size distribution analyser (HORIBA) LA-920, with relative refractive index as 200A000I.

Mode diameters of both Example Items 1 and 3 are approximately 5.5-5.7 μm, while particle diameters of Comparative Example items 1, 3 and 4 are decreased to approximately 3.2-3.7 μm. Moreover, as for Comparative Example Items 3 and 4, the rates of particle diameter equal to or less than 3.9 μm are as high as 39%, 52%, 54%, while as for Example Items 1 and 3, the rates are lower than half of these, that is 16.7% and 5.8%. Thus, the cell wall shapes are disrupted in Comparative Example Items while remained in Example Items.

Example 25

(Film Forming Property)

The film forming property of the Example Items and Comparative Example Items were measured. Data are the results of the measurement for each samples performed twice.

Example Items 1-16, Comparative Example Item 7, and YCW showed good film forming property, and all of these were perfect films or films having crack in one part. However, Comparative Example Items 1-6 and 8-12 were all fine film fractions, and no film forming property was observed, and the measurement of physical values of films as follows was not possible.

Example 26

(Film Mechanical Property)

The film mechanical property was measure for the samples wherein the film forming property was good.

For the film to be evaluated, a slurry of about 2% dry material weight concentration, wherein 10% glycerin based on dry material weight is added, was prepared and 1.0 g based on dry material is poured into a 100 mm×100 mm polystyrene square-dish. This dish was dried for a full day, to generate a cast film and the samples were subjected to the following measurement for film mechanical property test.

The results are shown in Table 3, each level being an average level.

As it is shown in Table 3, compared to YCW of Example 11, Comparative Example Item 7, as the decolorizing treatment proceeded, the film strength improved. Especially, for Example Items 10 and 16, the film strength improved significantly, the tensile strength increased by nearly 5 times of YCW film, and for the film of the Comparative Example Item 7, more than two-fold improvement was observed in strength. The strength of tip plunging showing the strength toward the film membrane was 4.5-fold compared with YCW, 3-fold compared with Comparative Example Item 7. Furthermore, elongation rate showing the flexibility of the film or the plunged depth of tip plunging increased as well.

TABLE 3

Film forming property and film mechanical property

| sample | film forming property | tensile strength at break (MPa) | elongation rate (%) | strength of tip plunging (N) | plunged depth (mm) |
|---|---|---|---|---|---|
| YCW (of Example 11) | ◎ | 13.6 | 4.0 | 4.1 | 2.2 |
| Comparative Example Item 7 | ◎ | 29.9 | 5.1 | 5.9 | 2.6 |
| Example Item 11 | ○ | 38.9 | 5.2 | 8.0 | 2.9 |
| Example Item 12 | ◎ | 54.1 | 5.2 | 8.1 | 3.2 |
| Example Item 15 | ◎ | 54.0 | 6.2 | 16.8 | 3.6 |
| Example Item 16 | ◎ | 64.4 | 6.5 | 18.1 | 3.6 |
| Example Item 10 | ◎ | 71.0 | 6.3 | 20.4 | 4.0 |
| Comparative Example Item 8 | x | estimation N.A. | → | → | → |
| Comparative Example Item 9 | x | N.A. | → | → | → |
| Comparative Example Item 10 | x | N.A. | → | → | → |
| Comparative Example Item 11 | x | N.A. | → | → | → |
| Comparative Example Item 12 | x | N.A. | → | → | → |

→: estimation N.A.

Example 27

(Preparation of Yeast Cell Wall Fractions (YCW-2) from Dried Yeast)

According to the method described in U.S. Pat. No. 3,349,677, dried brewer's yeast in a died condition obtained as a by-product material of the brewing process was suspended so that the solid content became 10 wt %. The yeast was treated with 100 MPa-homogenizer, and the internal cell components were dissolved with protease (NOVO; reacted by using Neutrase, Alkalase, at 45-60° C. at pH 7.5 for 15 hours). The cell residues obtained by removing soluble internal cell components by centrifuging (4200 rpm, 10 min) were washed with water to generate yeast cell wall fractions. The pH at this moment was about 7.0. Hereinafter, the fractions, i.e. yeast cell wall is abbreviated as YCW-2 (liquid YI:75).

(Ozone Treatment of YCW-2)

Ozone was injected to 1 L of 5% slurry of YCW-2 adjusted to pH 4 with 4 N hydrochloric acid, under the condition of pressure 0.1 MPa, liquid temperature 10° C., and ozone treatment was performed for 1 hour. An oxygen/ozone mixture gas generated with commercial electric discharged-type ozonizer by supplying oxygen from an oxygen cylinder was used as ozone gas. The gas was injected under the condition of pressure of 0.11 MPa, flow rate 2 L/min, ozone concentration 4.5% (w/w), and the ozone gas became in form of fine bubbles and a gas-liquid reaction was conducted. After the completion of ozone treatment, YCW slurry was adjusted to pH11 with 25% sodium hydroxide solution, and water-washing by centrifugation was performed twice with the condition of 4200 rpm, 10 min to obtain precipitated fractions.

(Hydrogen Peroxide Treatment After the Ozone Treatment of YCW-2)

The precipitated fractions were adjusted to a slurry of 2.5% dry material concentration of, 1% hydrogen peroxide concentration, and pH 10 with 25% sodium hydroxide, and reacted at 60° C. for 2 hours. After the reaction, centrifugation at 4200 rpm was conducted for 10 min, and the centrifuged precipitates were diluted with water and adjusted to a slurry of about 3% dry material concentration. The slurry was adjusted to pH 7-7.5 with 4N hydrochloric acid, to which 0.05-0.1% catalase (Nagase Chemtex, REYONET F PLUS) was added, stirred for 30 min and after the remaining oxygen hydroxide was degraded and removed, water-washing by centrifugation was performed twice. The obtained fractions were adjusted to pH 3.8, and the fractions were named as Example Item 27.

The liquid YI of the Example Item 27 was 0, with film property (10 ml/m$^2$·d·MPa), with film disintegration property (within 30 min).

Example 28

(Ethanol Treatment)

The precipitated fractions of Example 27, before adjusted to final pH 3.8, and ethanol were mixed at a weight ratio of 1:1, and the mixture was stirred for 30 min and water-washed twice by centrifugation. Thus obtained precipitated fractions were adjusted to pH 3.8, and used as Example Item 28. The liquid YI of the Example Item 28 was 0, with film property (10 ml/m$^2$·d·MPa), with film disintegration property (within 30 min).

Example 29

(Preparation of AYC-2 from Dried Yeast)

According to the method described in U.S. Pat. No. 3,349,677, YCW slurry adjusted to 5% YCW-2 dry material concentration and 0.3N hydrochloric acid concentration was maintained at 80° C. for 10 min, water-washing by centrifugation was performed twice. The precipitated fractions were diluted into a slurry of about 5% dry material concentration, the pH was adjusted to 7.5, water-washing by centrifugation was performed twice again. The obtained precipitated fractions were adjusted to pH 3.8.

Hereinafter the fractions are referred to as AYC-2. The liquid YI was 82.

(Ozone Treatment of AYC-2)

The above-mentioned AYC-2 was subjected to a preparation treatment similar to that described in Example 27 (ozone treatment followed by alkaline treatment), water-washed by centrifugation twice with the condition of 4200 rpm, 10 min to obtain precipitated fractions.

(Hydrogen Peroxide Treatment After the Ozone Treatment of AYC-2)

The precipitated fractions were adjusted to slurry of 2.5% dry material concentration, 1% hydrogen peroxide concentration, and pH 10 with 25% sodium hydroxide, and reacted at 60° C. for 2 hours. After the reaction, centrifugation at 4200 rpm was conducted for 10 min, and the centrifuged precipitates were diluted with water and adjusted to a slurry of about 3% dry material concentration. The slurry was adjusted to pH 7-7.5 with 4N hydrochloric acid, 0.05-0.1% catalase (Nagase Chemtex) was added, stirred for 30 min and after the remaining oxygen hydroxide was degraded and removed, water-washing by centrifugation was performed twice. The obtained fractions were adjusted to pH 3.8, and the fractions were named as Example Item 29. The liquid YI of the Example Item 29 was 0, with film property (10 ml/m$^2$·d·MPa), with film disintegration property (within 30 min).

Example 30

(Ethanol Treatment)

The precipitated fractions before adjusted to the final pH 3.8 of Example 29 and ethanol were mixed at a weight rate of 1:1, dispersed by stirring, after being a slurry form, stirred for 30 min, water-washed by centrifugation twice and the obtained precipitated fractions were adjusted to pH 3.8, to make Example Item 30. The liquid YI of the Example Item 30 was 0, with film property (10 ml/m$^2$·d·MPa), with film disintegration property (within 30 min).

Example 31

(Measurement of Component Composition (General 3 Components)

The comparison of components with various Example Items or Comparative Example Items of the present invention are shown (Table 4). As shown in Table 4, the Example Items showed trend that the protein or lipid levels are rather decreased compared with those of the Comparative Examples Item.

TABLE 4

| | Composition of 3 components | | |
|---|---|---|---|
| samples | ash d.m. % | lipid d.m. % | crude protein d.m. % |
| Example Item 1 | 1.1 | 7.5 | 9.3 |
| Example Item 2 | 1.0 | 1.9 | 10.9 |
| Example Item 3 | 1.3 | 6.3 | 1.3 |
| Example Item 4 | 2.1 | 15.5 | 9.3 |
| Example Item 6 | 0.14 | 1.5 | 3.2 |
| Example Item 7 | 1.29 | 15.6 | 5.2 |
| Example Item 8 | 1.31 | 3.24 | 9.06 |
| Example Item 9 | 1.11 | 2.63 | 1.62 |
| Example Item 10 | 0.62 | 1.16 | 2.64 |
| YCW (of Example 11) | 17.56 | 4.11 | 20.27 |
| Example Item 11 | 3.03 | 10.56 | 11.64 |
| Example Item 12 | 3.41 | 2.82 | 9.60 |
| Example Item 13 | 2.95 | 1.90 | 7.89 |
| Example Item 15 | 3.34 | 2.57 | 2.16 |
| Example Item 16 | 3.31 | 1.39 | 2.00 |
| Comparative Example Item 3 | 0.43 | 2.0 | 2.8 |
| Comparative Example Item 4 | 0.05 | 0.0 | 2.9 |
| Comparative Example Item 5 | 1.0 | 11.9 | 11.6 |
| Comparative Example Item 6 | 1.0 | 8.9 | 15.8 |
| Comparative Example Item 7 | 1.13 | 5.22 | 16.22 |
| Comparative | 34.89 | 5.53 | 2.16 |

TABLE 4-continued

Composition of 3 components

| samples | ash d.m. % | lipid d.m. % | crude protein d.m. % |
|---|---|---|---|
| Example Item 9 Comparative Example Item 10 | 10.84 | 12.34 | 5.12 |
| Comparative Example Item 11 | 1.06 | 6.74 | 2.14 |
| Comparative Example Item 12 | 1.27 | 3.54 | 2.02 |
| Comparative Example Item 13 | 0.14 | 5.31 | 3.26 |
| YCW-2 (of Example 27) | 4.81 | 1.78 | 41.75 |
| Example Item 28 | 3.49 | 0.91 | 5.11 |
| Example Item 30 | 0.45 | 1.05 | 5.27 |
| AYC-2 (of Example 29) | 0.81 | 2.87 | 33.31 |

Example 32

(Measurement of Sugar Composition)

Saccharides contained in yeast cell wall (derived from *Saccharomyces cerevisiae*) are mostly glucan and mannnan, and a small amount of chitin is contained near budding scar. To measure the sugar composition of yeast cell wall, the content of glucan/mannnan were hydrolyzed to glucose and mannose of composing monosaccharide to measure the contained amount in various Example Items or Comparative Example Items of the present invention.

As the composing monosaccharide is reductive sugar, according to the procedure of Tables 5 and 6, post-column method with high performance liquid chromatograph (hereinafter HPLC) was used to measure each sample as n=1.

TABLE 5

Method for preparing test solution

| 1 | preparing sample | 3-6 g of slurry of yeast cell wall fraction is dried with boiling water and crushed. |
| 2 | preparing sample | 4 ml of 72% sulfuric acid is added, and then 112 ml of water is added. |
| 3 | hydrolysis | 121° C., 1 hour |
| 4 | neutralization | with 25% NaOH, adjusted to pH 7-7.5 |
| 5 | filtration | filter No. 5→ membrane filter (pore size 0.45 μm) |

TABLE 6

Measuring condition: HPLC condition

| | model; condition, etc. | model; maker |
|---|---|---|
| HPLC | LC-10Advp | Shimadzu Corporation |
| detector | Spectro photo fluorometer | Shimadzu Corporation |
| column | TSKgel SUGAR AXI Ø 4.6 mm × 150 mm | TOSO |
| column temperature | 60° C. | |
| mobile phase | 0.5 mol/L borate buffer (pH 8.7) | |
| mobile phase flow rate | 0.4 ml/min | |
| fluorescence excitation wavelength | 320 nm | |
| fluorescence measurement wavelength | 430 nm | |

TABLE 6-continued

Measuring condition: HPLC condition

| | model; condition, etc. | model; maker |
|---|---|---|
| post-column | reaction reagent: 1 w/v % L-arginine solution reaction solution flow rate: 0.7 ml/min reaction temperature: 150° C. | |

As it is shown in Table 7, as a result of the sugar composition analysis, as the white color increase, glucan rate increases and the mannan content decrease. However, as for sample having film forming property, it was confirmed that mannan remained. On the other hand as for Comparative Example Items 8-12 having no film forming property, no mannose equivalent to mannan was detected.

TABLE 7

List of sugar compositions

| samples | glucose % | mannose % | glucose % + mannose % | glucose/ mannose |
|---|---|---|---|---|
| YCW (of Example 11) | 41.3% | 25.6% | 66.9% | 1.61 |
| Comparative Example Item 7 | 54.1% | 20.7% | 74.8% | 2.61 |
| Example Item 11 | 68.8% | 1.6% | 70.4% | 43.00 |
| Example Item 12 | 58.1% | 20.6% | 78.7% | 2.82 |
| Example Item 13 | 83.6% | 6.4% | 90.0% | 13.06 |
| Example Item 15 | 68.4% | 5.6% | 74.0% | 12.21 |
| Example Item 16 | 73.7% | 5.1% | 78.8% | 14.45 |
| Example Item 9 | 89.4% | 2.0% | 91.4% | 44.70 |
| YCW-2 (of Example 27) | 24.7% | 18.7% | 43.4% | 1.32 |
| Example Item 28 | 73.3% | 1.5% | 74.8% | 48.87 |
| AYC-2 (of example 29) | 21.5% | 36.7% | 58.2% | 0.59 |
| Example Item 30 | 85.1% | 1.3% | 86.4% | 65.46 |
| Comparative Example Item 8 | 81.8% | 0.0% | 81.8% | ∞ |
| Comparative Example Item 9 | 67.1% | 0.0% | 67.1% | ∞ |
| Comparative Example Item 10 | 69.3% | 0.0% | 69.3% | ∞ |
| Comparative Example Item 11 | 86.7% | 0.0% | 86.7% | ∞ |
| Comparative Example Item 12 | 91.7% | 0.0% | 91.7% | ∞ |

INDUSTRIAL APPLICABILITY

The decolorized yeast cell wall fractions of the present invention have a white color (e.g liquid YI 13 or less), as the color of yellow-brown to brown of the conventional yeast cell wall fractions is decolorized. The demerits before being decolorized have been improved and they afford a nonsticky finish despite its viscosity, thus the coated particles and/or granules are not aggregated. Moreover, they have an extremely low oxygen permeability coefficient, a function to control release time, and show no change for film property even after treatment with organic solvent (methanol, etc.).

Furthermore, the present invention can be used as an excellent coating agent for food products, food product materials, pharmaceutical, enzyme, microorganisms, seeds, agrochemicals, fertilizers, flavors or pigments and the like, by using the decolorized yeast cell wall fractions which have the above mentioned properties produced with the present invention as primary components, and by adding plasticizers, oxygen-barrier property enhancers, and the like. The coating agent of the present invention has an excellent effect to prevent volatilization and sublimation of internal components. For example, it is useful as an inhibitor of volatilization or sublimation of agents containing volatile or sublimate substances, being a problem of "generation of whisker" in the field of medicinal preparation.

The invention claimed is:

1. A decolorized yeast cell wall fraction prepared by decolorizing cell residue obtained by removing internal soluble cell components from enzyme-treated yeast, or cell residue obtained by further treating the cell residue with acid solution and removing acid solution-soluble components, by using a decolorizing agent, and washing with water or organic solvent;
   whose yellow index (YI) of the liquid measured by a reflective method with the use of SE-2000 of Nippon Denshoku, with illumination C, field of view 2 degree, is 13 or less;
   and whose oxygen permeability is 250 ml/$m^2$d MPa or less at a humidity of 60% RH when 5% (weight ratio) slurry of the decolorized yeast cell wall fraction is cast using a baker applicator, on an oriented-polypropylene film Senesi-POP of Daicel Chemical Industries, at a film membrane thickness of 0.02 mm, dried for 45 minutes in an oven at 60° C. to make a casting film whose film membrane thickness is approximately 0.015 mm;
   said decolorized yeast cell wall fraction having a cell wall retaining property, and having a property to form continuous film;
   wherein a disintegration time of the continuous film formed from the decolorized yeast cell wall fraction in pure water is within 60 minutes when 5% (weight ratio) slurry of the decolorized yeast cell wall is dried for 2 hours at 60° C. in a circular container with a diameter of 60 mm to make a casting film with a film membrane thickness of approximately 0.1 mm.

2. A method for producing the a decolorized yeast cell wall fraction, the method comprising:
   decolorizing cell residue which is obtained by removing internal soluble cell components from enzyme-treated yeast, or cell residue which is obtained by further treating the cell residue with acid solution and removing acid solution-soluble components, by using a decolorizing treatment with a decolorizing agent; and
   washing the decolorized cell residue with water or organic solvent.

3. A coating agent whose primary component is the decolorized yeast cell wall fraction according to claim 1.

4. The method for producing the decolorized yeast cell wall fraction according to claim 2, wherein the decolorizing treatment with the decolorizing agent is a decolorizing treatment with hydrogen peroxide and ozone.

5. The method for producing the decolorized yeast cell wall fraction according to claim 2, wherein the internal soluble cell components removed from the enzyme-treated yeast are removed by treating the yeast with one or more enzymes selected from the group consisting of proteases, nucleases, β-glucanase, esterases, lipases, and phosphatase which are commonly used in the manufacture of common yeast extract.

6. The method for producing the decolorized yeast cell wall fraction according to claim 2, wherein the further treatment of the cell residue with acid solution is a treatment with a solution of an acid selected from the group consisting of hydrochloric acid, sulfuric acid, nitric acid, and an organic acid selected from the group consisting of acetic acid and citric acid.

7. The method of producing the decolorized yeast cell wall fraction according to claim 4, wherein the decolorizing treatment with a decolorizing agent is a decolorizing treatment with ozone and then hydrogen peroxide.

* * * * *